United States Patent
Rama et al.

(10) Patent No.: US 11,954,908 B2
(45) Date of Patent: Apr. 9, 2024

(54) COMMUNICATION SUPPORT DEVICE, COMMUNICATION SUPPORT METHOD, COMPUTER-READABLE STORAGE MEDIUM INCLUDING PROGRAM, AND SERVER

(71) Applicant: OMRON Corporation, Kyoto (JP)

(72) Inventors: Endri Rama, Kyoto (JP); Kazuo Yamamoto, Kyoto (JP); Tomohiro Yabuuchi, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 263 days.

(21) Appl. No.: 17/391,615

(22) Filed: Aug. 2, 2021

(65) Prior Publication Data

US 2022/0036077 A1  Feb. 3, 2022

(30) Foreign Application Priority Data

Aug. 3, 2020 (JP) ................................. 2020-131580

(51) Int. Cl.
*G06V 20/20* (2022.01)
*A61F 9/08* (2006.01)
(Continued)

(52) U.S. Cl.
CPC ............... *G06V 20/20* (2022.01); *A61F 9/08* (2013.01); *G06T 7/70* (2017.01); *G06V 40/174* (2022.01); *G08B 6/00* (2013.01); *G10L 13/02* (2013.01)

(58) Field of Classification Search
CPC .... G06V 20/20; G06V 40/174; G06V 40/171; A61F 9/08; G06T 7/70;
(Continued)

(56) References Cited

U.S. PATENT DOCUMENTS 11,576,817 B1 * 2/2023 Creasy ............... G01C 21/3629
11,580,727 B2 * 2/2023 Wexler ................... G06V 40/20
(Continued)

FOREIGN PATENT DOCUMENTS

| CN | 108836769 A | 11/2018 |
| JP | 2000126160 A | 5/2000 |
| JP | 2004127285 A | 4/2004 |

OTHER PUBLICATIONS

JPO Notice of Reasons for Refusal for corresponding JP Application No. 2020-131580; dated Feb. 13, 2024; 6 pages.

*Primary Examiner* — Wesley J Tucker
(74) *Attorney, Agent, or Firm* — CANTOR COLBURN LLP

(57) ABSTRACT

The communication support device includes a position acquisition unit, an imaging unit, a storage, a category ranking setting unit, a counterpart detector, and a notification unit. The position acquisition unit acquires position information indicating a position of a user. The imaging unit captures an image of a surrounding environment of the user to acquire a captured image. The storage stores the counterpart database. In the counterpart database, an image of a counterpart and a category indicating a property of the counterpart are associated with the counterpart. The category ranking setting unit sets a priority to the category according to the position information acquired by the position acquisition unit. The counterpart detector detects a counterpart belonging to the category in the captured image in order of the priority set by the category ranking setting unit. The notification unit notifies the user of information regarding the counterpart detected by the counterpart detector.

9 Claims, 25 Drawing Sheets

(51) Int. Cl.
*G06T 7/70* (2017.01)
*G06V 40/16* (2022.01)
*G08B 6/00* (2006.01)
*G10L 13/02* (2013.01)

(58) Field of Classification Search
CPC . G06T 2207/10016; G06T 2207/30196; G06T 2207/30201; G08B 6/00; G08B 21/22; G10L 13/02
See application file for complete search history.

(56) References Cited

U.S. PATENT DOCUMENTS

| | | | |
|---|---|---|---|
| 11,710,387 B2* | 7/2023 | Goulden | H04M 11/025 |
| | | | 382/118 |
| 2003/0063776 A1* | 4/2003 | Sato | A61F 9/08 |
| | | | 382/106 |
| 2004/0109587 A1 | 6/2004 | Segawa et al. | |
| 2008/0085037 A1 | 4/2008 | Segawa et al. | |
| 2011/0092249 A1* | 4/2011 | Evanitsky | H04M 1/72481 |
| | | | 455/556.1 |
| 2014/0253701 A1* | 9/2014 | Wexler | G06F 1/163 |
| | | | 348/62 |
| 2014/0267651 A1* | 9/2014 | Wexler | G10L 13/00 |
| | | | 348/62 |
| 2015/0198455 A1* | 7/2015 | Chen | G01C 21/3623 |
| | | | 701/428 |
| 2021/0390333 A1* | 12/2021 | Rama | G06F 3/167 |

* cited by examiner

Fig.3
51
| ID | IMAGE | NAME | CATEGORY | ADDRESS | TEL | E-MAIL | RELATIONSHIP COEFFICIENT |
|---|---|---|---|---|---|---|---|
| 1 |  | A | FAMILY | ... | ... | ... | 1 |
| 2 |  | B | FAMILY | ... | ... | ... | 0.75 |
| 3 |  | C | WORKPLACE | ... | ... | ... | 0.5 |
| 4 |  | D | FRIEND | ... | ... | ... | 0.4 |
| 5 |  | E | FRIEND | ... | ... | ... | 0.3 |
| 6 |  | F | NEIGHBOR | ... | ... | ... | 0.3 |
| 7 |  | G | RELATIVE | ... | ... | ... | 0.2 |
| 8 |  | H | OTHERS | ... | ... | ... | 0.2 |
| 9 |  | ROBOT 1 | OTHERS | ... | ... | ... | 0.3 |

| No | CATEGORY | RANK |
|----|----------|------|
| 1 | FRIEND | 1 |
| 2 | RELATIVE | 2 |
| 3 | WORKPLACE | 3 |
| 4 | NEIGHBOR | 4 |
| 5 | FAMILY | 5 |
| 6 | OTHERS | 6 |

| No | CATEGORY | RANK |
|----|----------|------|
| 1 | FRIEND | 2 |
| 2 | RELATIVE | 4 |
| 3 | WORKPLACE | 1 |
| 4 | NEIGHBOR | 6 |
| 5 | FAMILY | 5 |
| 6 | OTHERS | 3 |

| No | CATEGORY | RANK | | | |
|---|---|---|---|---|---|
| | | INITIAL VALUE | WORKPLACE AREA | HOME AREA | ... |
| 1 | FRIEND | 1 | 2 | 4 | ... |
| 2 | RELATIVE | 2 | 4 | 3 | ... |
| 3 | WORKPLACE | 3 | 1 | 5 | ... |
| 4 | NEIGHBOR | 4 | 6 | 2 | ... |
| 5 | FAMILY | 5 | 5 | 1 | ... |
| 6 | OTHERS | 6 | 3 | 6 | ... |

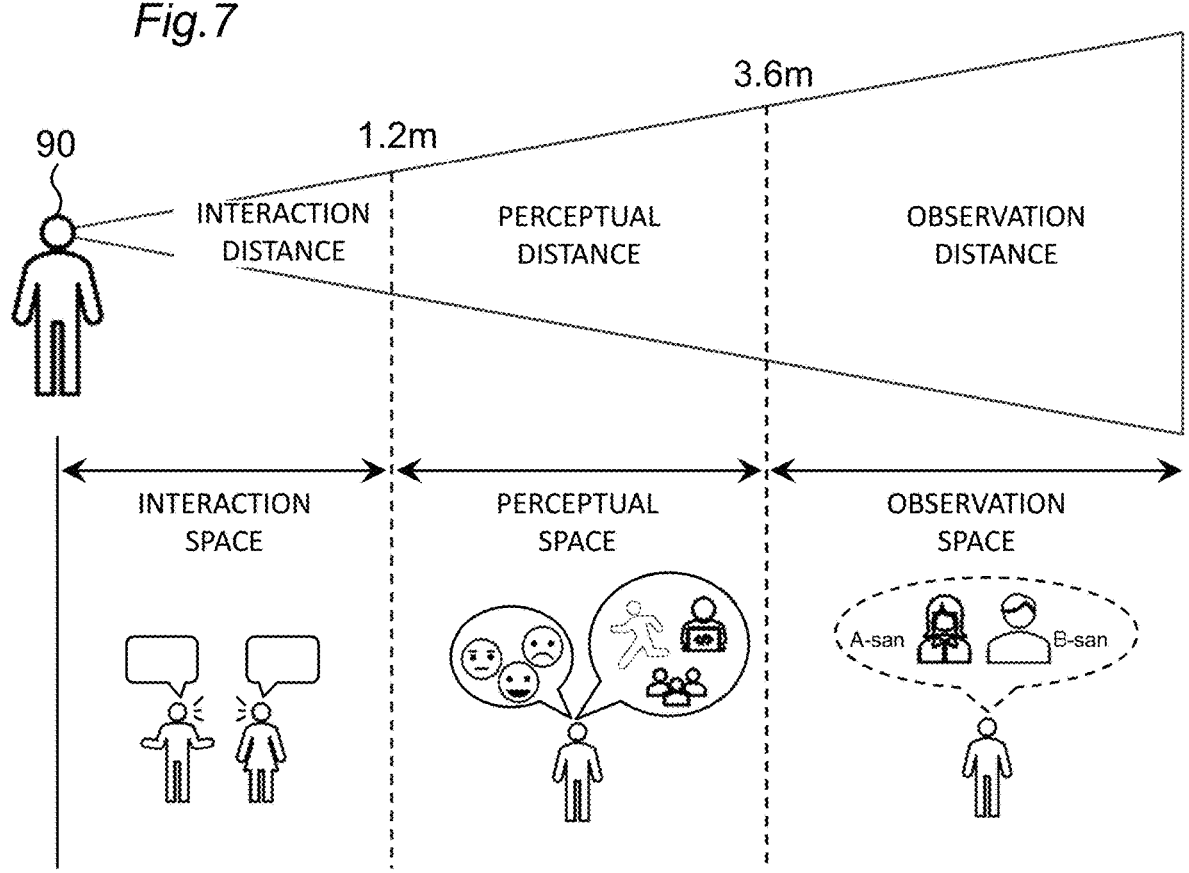

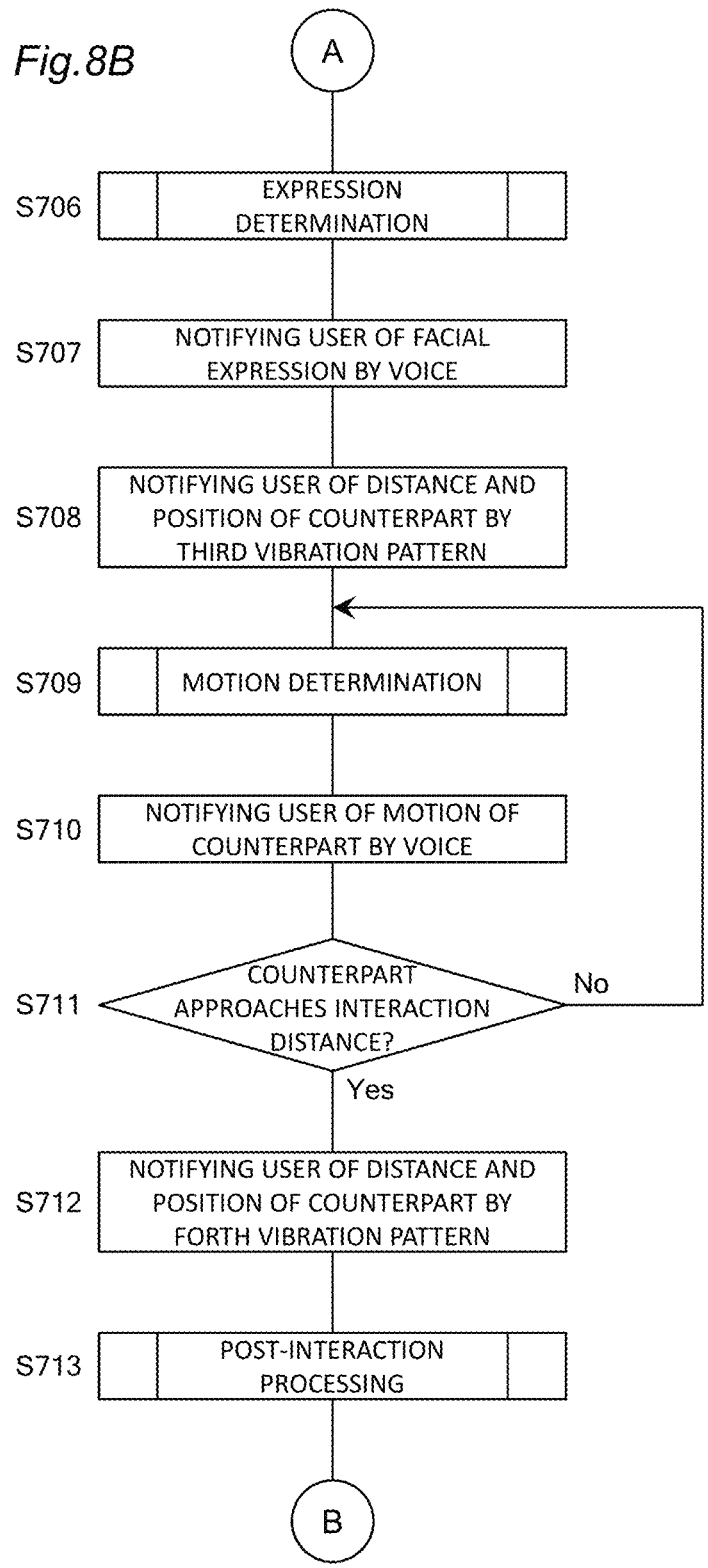

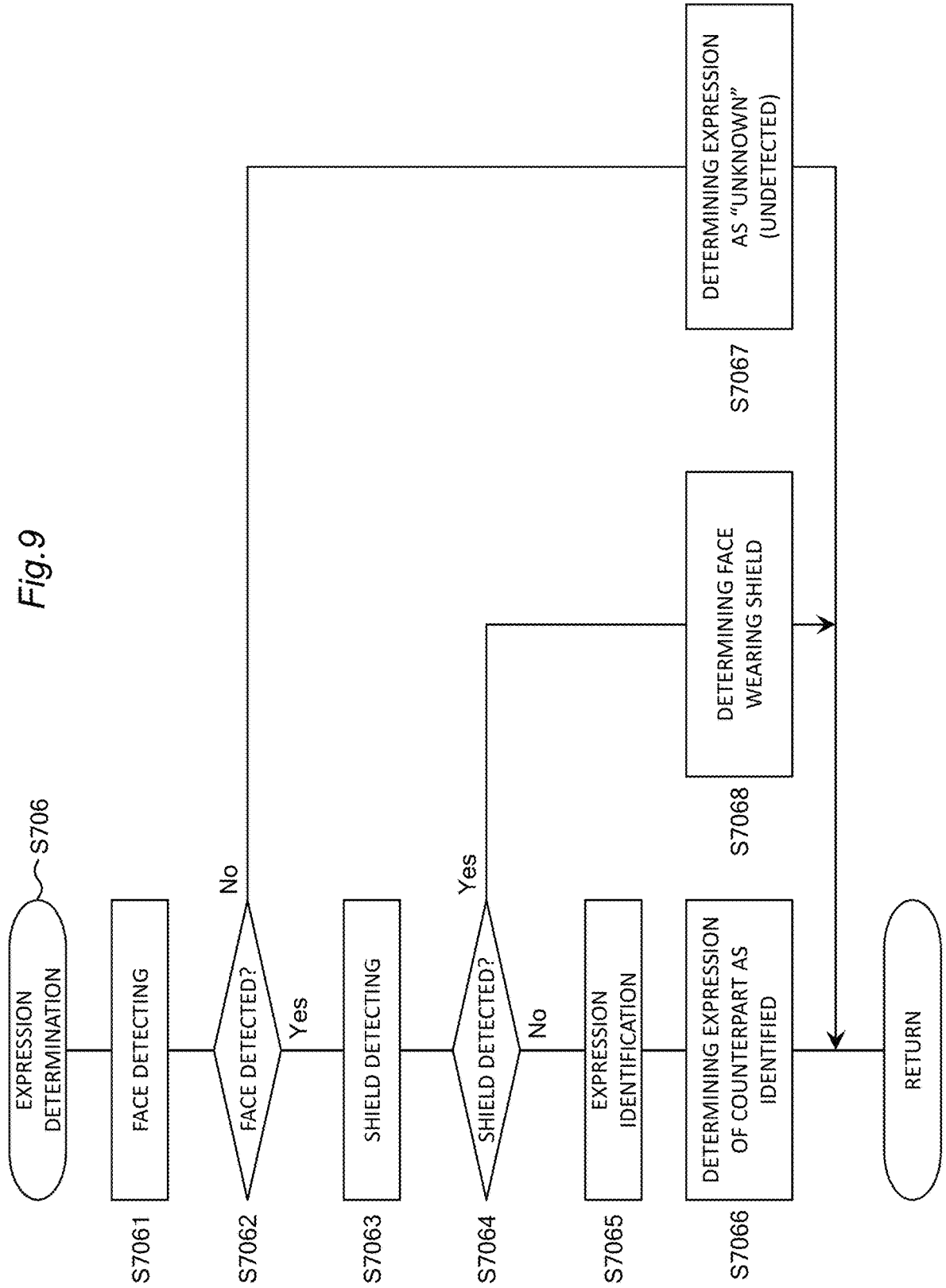

Fig.21
51a
| ID | IMAGE | NAME | CATEGORY |
|---|---|---|---|
| 1 |  | A | BUILDING 401 |
| 2 |  | B | BUILDING 405 |
| 3 |  | C | BUILDING 405 |
| 4 |  | D | BUILDING 403 |
| 5 |  | E | BUILDING 404 |
| 6 |  | F | BUILDING 402 |
| 7 |  | G | BUILDING 404 |
| 8 |  | H | OTHERS |
| 9 |  | ROBOT 1 | BUILDING 401 |

| CATEGORY | RANK |
|---|---|
| BUILDING 401 | 1 |
| BUILDING 402 | 2 |
| BUILDING 403 | 3 |
| BUILDING 404 | 4 |
| BUILDING 405 | 5 |
| OTHERS | 6 |

50g

| CATEGORY | RANK |
|---|---|
| BUILDING 402 | 1 |
| BUILDING 401 | 2 |
| BUILDING 403 | 3 |
| BUILDING 404 | 4 |
| BUILDING 405 | 5 |
| OTHERS | 6 |

COMMUNICATION SUPPORT DEVICE, COMMUNICATION SUPPORT METHOD, COMPUTER-READABLE STORAGE MEDIUM INCLUDING PROGRAM, AND SERVER

CROSS-REFERENCE TO RELATED APPLICATIONS

The present invention claims priority under 35 U.S.C. § 119 to Japanese Patent Application No. 2020-131580 filed on Aug. 3, 2020, the entire content of which is incorporated herein by reference.

TECHNICAL FIELD

The present disclosure relates to a communication support device, a communication support method, a computer-readable storage medium including a program, and a server.

BACKGROUND ART

Chinese Patent Application Publication No. 108836769 discloses a device and a method for assisting movement of a visually impaired person. This device acquires an image by a visual sensor of an obstacle detection module, detects a person, an obstacle, and the like in the image by image analysis, and performs feedback by a voice.

When a counterpart, such as an acquaintance of a user, appears in the image, the user can smoothly communicate with the counterpart by receiving an identification result of the counterpart by a technique such as image analysis. However, it takes time for the device to access a database and detect a person or an object appearing in the image, the response time increases, and it is difficult for the user to smoothly communicate with the counterpart in some cases.

SUMMARY

An object of the present disclosure is to provide a communication support means for reducing the time required to detect a counterpart.

A communication support device according to an aspect of the present disclosure includes: a position acquisition unit that acquires position information indicating a position of a user; an imaging unit that captures an image of a surrounding environment of the user to acquire a captured image; a storage that stores a counterpart database in which an image of a counterpart and a category indicating a property of the counterpart are associated with the counterpart; a category ranking setting unit that sets a priority to the category according to the position information; a counterpart detector that detects a counterpart belonging to the category in the captured image in order of the priority set by the category ranking setting unit; and a notification unit that notifies the user of information regarding the counterpart detected by the counterpart detector.

A server according to another aspect of the present disclosure includes: a position acquisition unit that acquires position information indicating a position of a user; a counterpart database in which an image of a counterpart and a category indicating a property of the counterpart are associated with the counterpart; a category ranking setting unit that sets a priority to the category according to the position information; and a transmission unit that transmits information in the counterpart database and information indicating the priority set by the category ranking setting unit to a communication support device that detects the counterpart based on the information in the counterpart database and the information indicating the priority, and notifies the user of the detected counterpart.

A communication support method according to still another aspect of the present disclosure includes: causing a position acquisition unit to acquire position information indicating a position of a user; causing an imaging unit to capture an image of a surrounding environment of the user to acquire a captured image; storing a counterpart database in which an image of a counterpart and a category indicating a property of the counterpart are associated with the counterpart, in a storage; causing a category ranking setting unit to set a priority to the category according to the position information; causing a counterpart detector to detect a counterpart belonging to the category in the captured image in order of the priority set by the category ranking setting unit; and causing a notification unit to notify the user of information regarding the counterpart detected by the counterpart detector.

The present invention can reduce the time required to detect the counterpart in the captured image when supporting the user to communicate with the counterpart based on the captured image.

BRIEF DESCRIPTION OF THE DRAWINGS

FIG. 3 is a table showing an example of a counterpart database stored in a storage of the communication support device illustrated in FIG. 2.

FIG. 4A is a table showing an example of category ranking information stored in the storage of the communication support device illustrated in FIG. 2.

FIG. 4B is a table showing another example of the category ranking information stored in the storage of the communication support device illustrated in FIG. 2.

FIG. 4C is a table showing still another example of the category ranking information stored in the storage of the communication support device illustrated in FIG. 2.

FIG. 7 is a schematic view for describing an example of a spatial distance.

FIG. 8B is a flowchart illustrating a detailed flow of the long distance flow illustrated in FIG. 5.

FIG. 9 is a flowchart illustrating a detailed flow of a facial expression determination processing step illustrated in FIG. 8B.

FIG. 21 is a table showing an example of a counterpart database in the modification of the embodiment of the present disclosure.

FIG. 22 is a table showing an example of category ranking information stored in a storage.

DETAILED DESCRIPTION

Hereinafter, embodiments of a communication support device according to the present disclosure will be described with reference to the accompanying drawings. Note that, the same components are denoted by the same reference signs in each of the following embodiments.

1. Application Example

Figure 1:
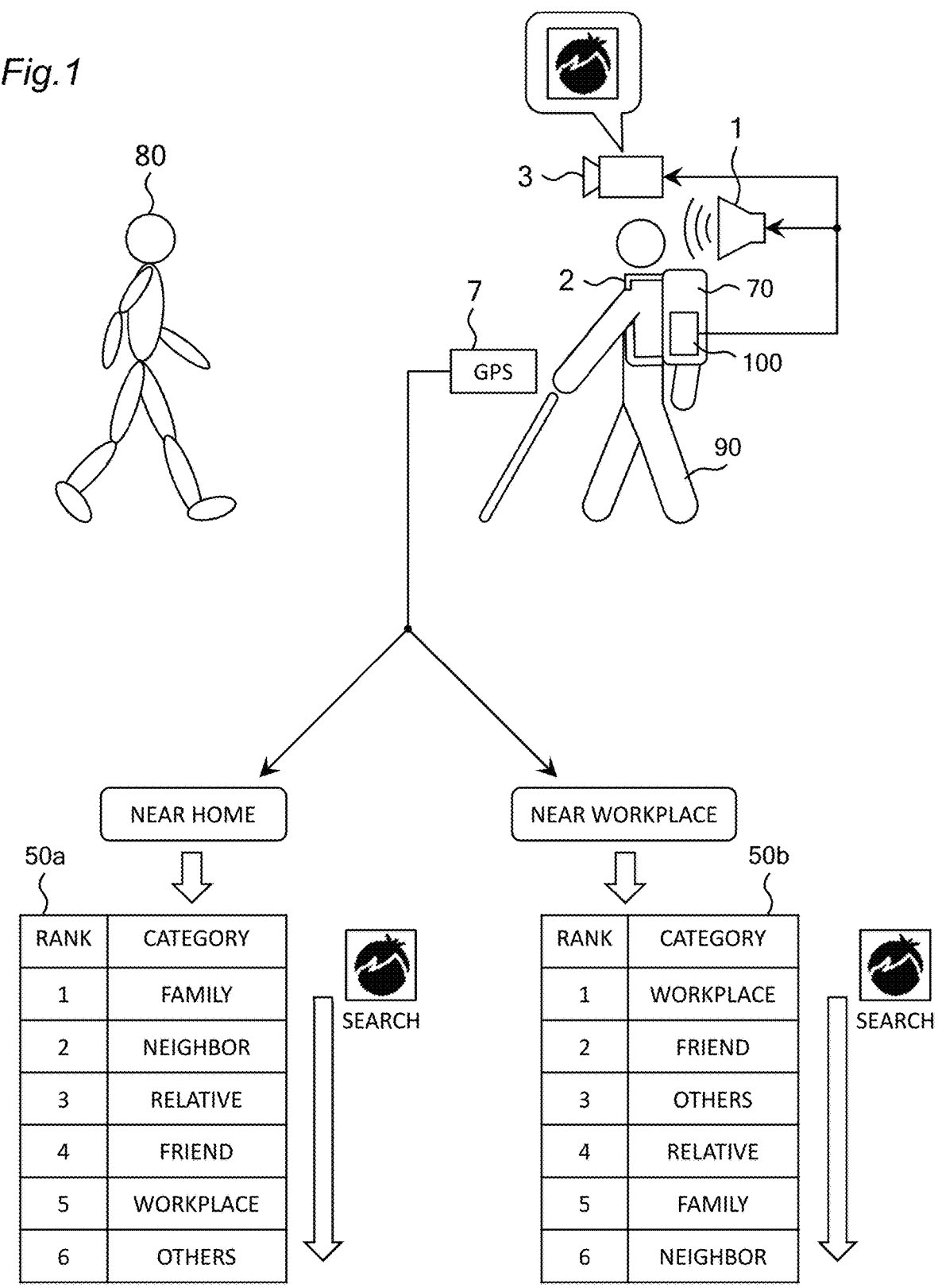
FIG. 1 is a schematic view illustrating an application example of a communication support device according to an embodiment of the present disclosure.

FIG. 1 is a schematic view illustrating an application example of a communication support device 100 according to the embodiment of the present disclosure. The communication support device 100 provides communication support to, for example, a user 90 who is a visually impaired person. It is difficult for the visually impaired person to visually perceive a figure, a face, and the like even if a counterpart 80 such as an acquaintance approaches. Therefore, it is difficult to recognize a name, a facial expression, a motion, and the like of the counterpart 80. Therefore, there is a case where the user 90 is not capable of taking a motion such as greeting the counterpart 80 even if the counterpart 80 approaches.

Therefore, the communication support device 100, for example, captures an image of the surroundings with a camera 3, analyzes a captured image to detect the counterpart 80, and outputs identification information such as a name of the counterpart 80 and information such as a position, a distance, a facial expression, a motion to notify the user 90. The communication support device 100 can execute personal recognition while the user 90 is taking a motion (for example, walking) and/or is stopped (is not taking any motion).

The communication support device 100 is mounted on a luggage such as a rucksack 70 of a user 90, for example. Alternatively, the communication support device 100 itself may be wearable. Information about a position of the counterpart 80 and a distance between the counterpart 80 and the user 90 can be notified to the user 90 by a vibration using a vibration unit 2. On the other hand, it is difficult to notify identification information such as a name, a facial expression, and a motion of the counterpart 80 by the vibration. For example, the user 90 is notified by a voice using a voice output unit 1 such as a speaker.

In order to detect the counterpart 80 as described above, for example, the communication support device 100 searches a counterpart database in which the counterpart such as an acquaintance is registered for a person matching or resembling a person appearing in the captured image. At this time, it may take a lot of time to detect the counterpart 80 if the counterpart database is searched randomly. Then, the response time of the communication support device 100 increases, and the user 90 is likely to pass the counterpart 80 while the voice output unit 1 detects the counterpart 80 and reads information regarding the counterpart 80. In this case, it is difficult for the user 90 to communicate smoothly with the counterpart 80.

Therefore, the communication support device 100 according to the present disclosure records, for example, the information regarding the counterpart 80 in the counterpart database in association with categories indicating properties of the counterpart 80. For example, as illustrated in FIG. 1, the categories include classifications such as a family, a workplace, a friend, a neighbor, a relative, and others. The communication support device 100 according to the present disclosure acquires position information indicating a position of the user 90 from, for example, a GPS receiver 7, and sets priorities to the categories according to the position information. For example, when the user 90 is near home of the user 90, priorities as illustrated in category ranking information 50a of FIG. 1 are assigned to the respective categories. When the user 90 is near a workplace of the user 90, priorities as illustrated in category ranking information 50b of FIG. 1 are assigned to the respective categories.

The communication support device 100 detects a counterpart belonging to a category in the captured image in order of priority. For example, when the user 90 is near the home of the user 90, the communication support device 100 first searches only for counterparts belonging to the category of "family", and detects one matching or resembling the person appearing in the captured image (see the category ranking information 50a in FIG. 1). Next, the communication support device 100 searches only for counterparts belonging to the category of "neighbor", and detects one matching or resembling the person appearing in the captured image. Hereinafter, the same applies to categories to which lower priorities have been assigned.

In this manner, the communication support device 100 detects the counterparts belonging to the category in the captured image in the order of the set priority. For example, the communication support device 100 searches the counterpart database for one matching or resembling the person appearing in the captured image in descending order of category ranking. As a result, the time required to detect the counterpart 80 can be reduced. If the counterpart 80 can be quickly detected, the notification unit 10 can quickly notify the user 90 of information. Therefore, the user 90 can quickly obtain information regarding the counterpart 80 present in the periphery, and can smoothly or naturally communicate with the counterpart 80.

2. First Embodiment

2-1. Configuration Example

Figure 2:
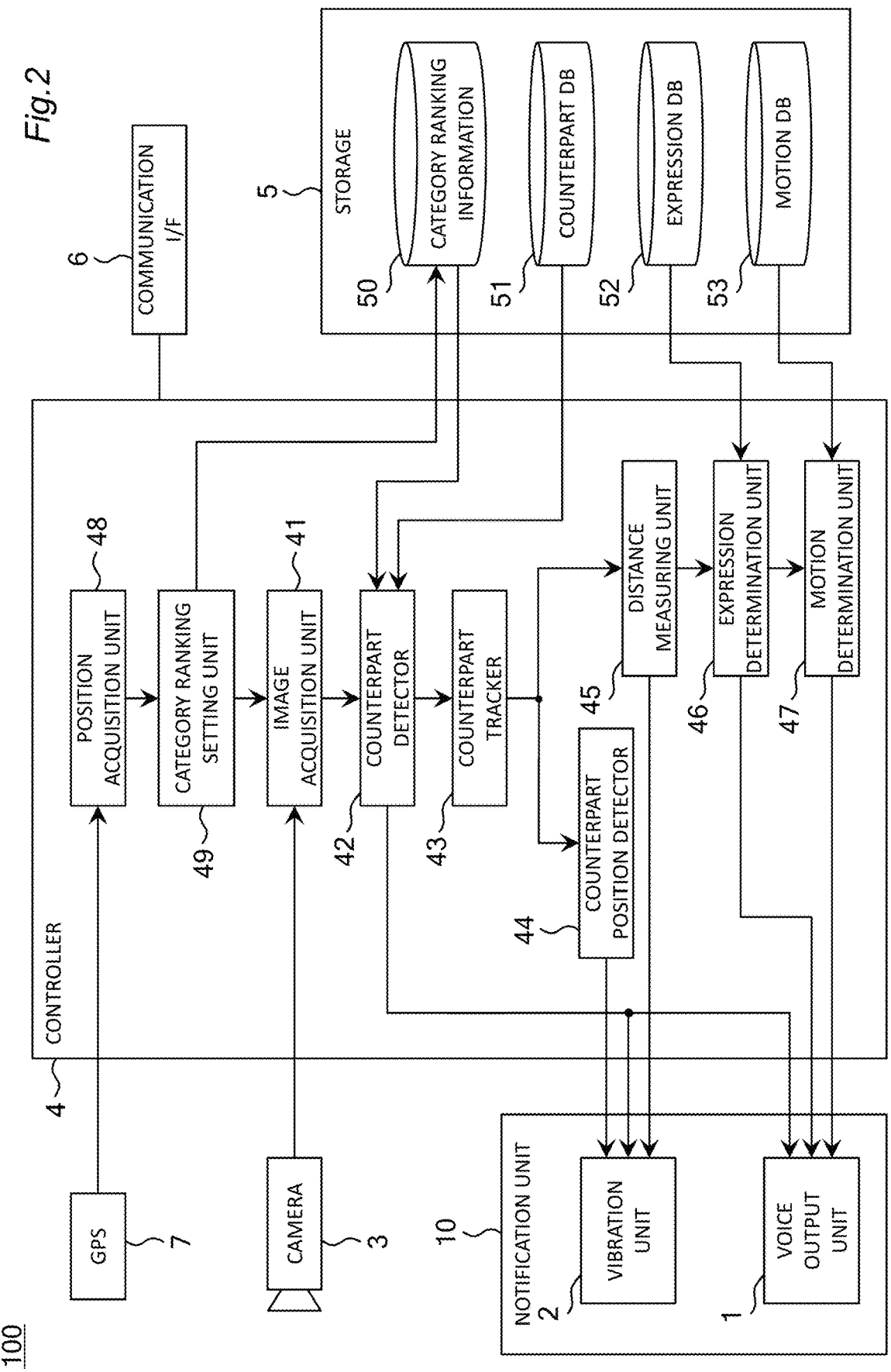
FIG. 2 is a block diagram illustrating a configuration example of the communication support device according to a first embodiment of the present disclosure.

FIG. 2 is a block diagram illustrating a configuration example of the communication support device 100 according to a first embodiment of the present disclosure. The communication support device 100 includes the global positioning system (GPS) receiver 7, the camera 3, a controller 4, a storage 5, a communication interface (I/F) 6, and a notification unit 10. The GPS receiver 7 is a positioning device that measures a position of the communication support device 100. The GPS receiver 7 is an example of a "positioning unit" of the present disclosure. The positioning unit includes, for example, a satellite positioning system such as a global navigation satellite system (GNSS) receiver. The GNSS includes, for example, a GPS. It suffices that the GPS receiver 7 can measure a position of the user 90, and may be mounted on an information processing device such as a mobile phone and a smartphone carried by the user 90.

The camera 3 is an imaging device that captures an image of a surrounding environment of the user 90 to form a captured image. The camera 3 is an example of an "imaging unit" of the present disclosure. The camera 3 captures an image of the periphery of the user 90 at a predetermined frame rate, for example, to sequentially generate image data. The camera 3 forms the captured image by, for example, a solid-state imaging element such as a complementary MOS (CMOS) and a charge coupled device (CCD). The camera 3 is, for example, a wearable camera that can be worn by the user 90. For example, the camera 3 is a spectacle-type camera mounted on spectacles, and captures a direction of a line of sight of the user 90. The camera 3 may be mounted on a luggage of the user 90 such as a rucksack and a suitcase.

The controller 4 includes a central processing unit (CPU), a random access memory (RAM), a read only memory (ROM), and the like, and is an information processing device that controls each component of the communication support device 100 according to information processing. The controller 4 includes, for example, a position acquisition unit 48, a category ranking setting unit 49, an image acquisition unit 41, a counterpart detector 42, a counterpart tracker 43, a counterpart position detector 44, a distance measuring unit 45, an expression determination unit 46, and a motion determination unit 47 as components. Processing in charge of each of the components of the controller 4 may be executed as the controller 4 executes a necessary program. Such a program may be stored in the storage 5. When the controller 4 executes a necessary program, a target program stored in the storage 5 is expanded in the RAM. The controller 4 controls each of the components by interpreting and executing the program expanded in the RAM using the CPU. An operation example of each of the components will be described later.

The communication interface 6 includes an interface circuit configured to enable a communication connection between the communication support device 100 and an external device. The communication interface 6 communicates according to standards such as IEEE802.3, IEEE802.11 or Wi-Fi (registered trademark), LTE, 3G, 4G, and 5G. The communication interface 6 may be an interface circuit that performs communication according to standards such as universal serial bus (USB), HDMI (registered trademark), IEEE1394, and Bluetooth (registered trademark).

The notification unit 10 is an output device configured to transmit information to the user 90. The notification unit 10 includes, for example, the voice output unit 1 and the vibration unit 2. The voice output unit 1 is, for example, an output device that outputs a voice according to control by the controller 4. The voice output unit 1 includes, for example, audio devices such as a speaker, an earphone, and a headphone. The vibration unit 2 is, for example, a vibrator that generates a vibration according to control by the controller 4.

In the embodiment, an example in which each function of the controller 4 is realized by the CPU will be described. However, some or all of the above functions may be realized by one or more dedicated processors. In addition, regarding the components of the controller 4, the functions may be omitted, replaced, or added as appropriate according to an embodiment. The controller 4 may be formed of various semiconductor integrated circuits such as a CPU, an MPU, a GPU, a microcomputer, a DSP, an FPGA, and an ASIC.

The storage 5 is a computer-readable storage medium that accumulates information such as a program by an electrical, magnetic, optical, mechanical or chemical operation so as to enable reading of information such as the program recorded by a computer or other devices, machine, and the like. The storage 5 is, for example, an auxiliary storage device such as a hard disk drive and a solid state drive. The storage 5 stores, for example, category ranking information 50, a counterpart database 51, an expression database 52, a motion database 53, a program executed by the controller 4, and the like. The storage 5 may include a main storage device such as a RAM. The storage of these pieces of data in the storage 5 is merely an example, and these pieces of data may be stored in, for example, an external server with which the communication support device 100 can communicate via the communication interface 6.

FIG. 3 is a table showing an example of the counterpart database 51 stored in the storage 5 of the communication support device 100 illustrated in FIG. 2. The counterpart database 51 stores information regarding a counterpart such as an identification number (ID) of the counterpart, an image including a face, a name, a category, a relationship coefficient, an address, a telephone number, an e-mail address, and a date of birth. The counterpart is a person who the user 90 wants to communicate with or a person who can communicate with the user 90, and includes, for example, an acquaintance of the user 90, a celebrity, and the like. As the counterpart, not only a person but also an object that can serve as a communication target, such as a robot, may be registered.

In FIG. 3, the category is, for example, a classification indicating a property of the counterpart. For example, the category is determined based on an address, a name or an address of a workplace, or the like of the counterpart. Such a category can be said to be a classification indicating a property related to the living area of the counterpart. Alternatively, for example, the category is a classification indicating a property of the counterpart based on a relationship between the counterpart and the user 90. For example, such a category includes, for example, classifications such as a family, a workplace, a friend, a neighbor, a relative, and the like. The workplace category may include classifications related to a workplace such as a boss, a subordinate, and a colleague. For example, the category is designated by the user 90 when the user 90 registers the counterpart in the counterpart database 51.

For example, each category can be associated with a particular place. For example, the family category, the neighbor category, and the like are associated with a place around the home. The friend category, the relative category may also be associated with a place around the home.

Similarly, for example, the workplace category is associated with a workplace address. Which category is associated with which place may be set in advance by the user 90 and recorded in, for example, the counterpart database 51.

In addition, in FIG. 3, the relationship coefficient is, for example, an index indicating the closeness of the relationship between the user 90 and the counterpart. The relationship coefficient is input in advance by the user 90 himself or herself, for example. The relationship coefficient may be determined based on the number of times of meeting between the user 90 and the counterpart, a blood relationship such as a parent, and the like. The relationship coefficient has a higher value as the relationship between the user 90 and the counterpart is closer, for example. The relationship coefficient is represented by, for example, a numerical value between 0 and 1.

FIG. 4A to FIG. 4C are tables showing examples of the category ranking information 50 stored in the storage 5 illustrated in FIG. 2. In the category ranking information 50, a ranking is set for each category included in the counterpart database 51 illustrated in FIG. 3. In category ranking information 50c illustrated in FIG. 4A, the first to sixth rankings are set to categories of a friend, a relative, a workplace, a neighbor, a family, and others, respectively. These rankings may be designated by the user 90 as initial values. The category ranking information 50 is updated from the initial values illustrated in FIG. 4A to category ranking information 50d illustrated in FIG. 4B, for example, in accordance with a change in a situation such as a position of the communication support device 100 or the user 90. In the category ranking information 50, rankings corresponding to positions of the communication support devices 100 or the users 90 may be stored in advance as illustrated in category ranking information 50e in FIG. 4C.

2-2. Operation Example 2-2-1. Overall Flow

The communication support device 100 according to the embodiment notifies the user 90 of a name, a position, a distance, and the like of a counterpart such as an acquaintance to support the user 90 to smoothly communicate with the counterpart. For example, the communication support device 100 supports the user 90 who is a visually impaired person to smoothly communicate with a counterpart such as an acquaintance. Hereinafter, an operation example of the communication support device 100 will be described with reference to FIG. 5.

Figure 5:
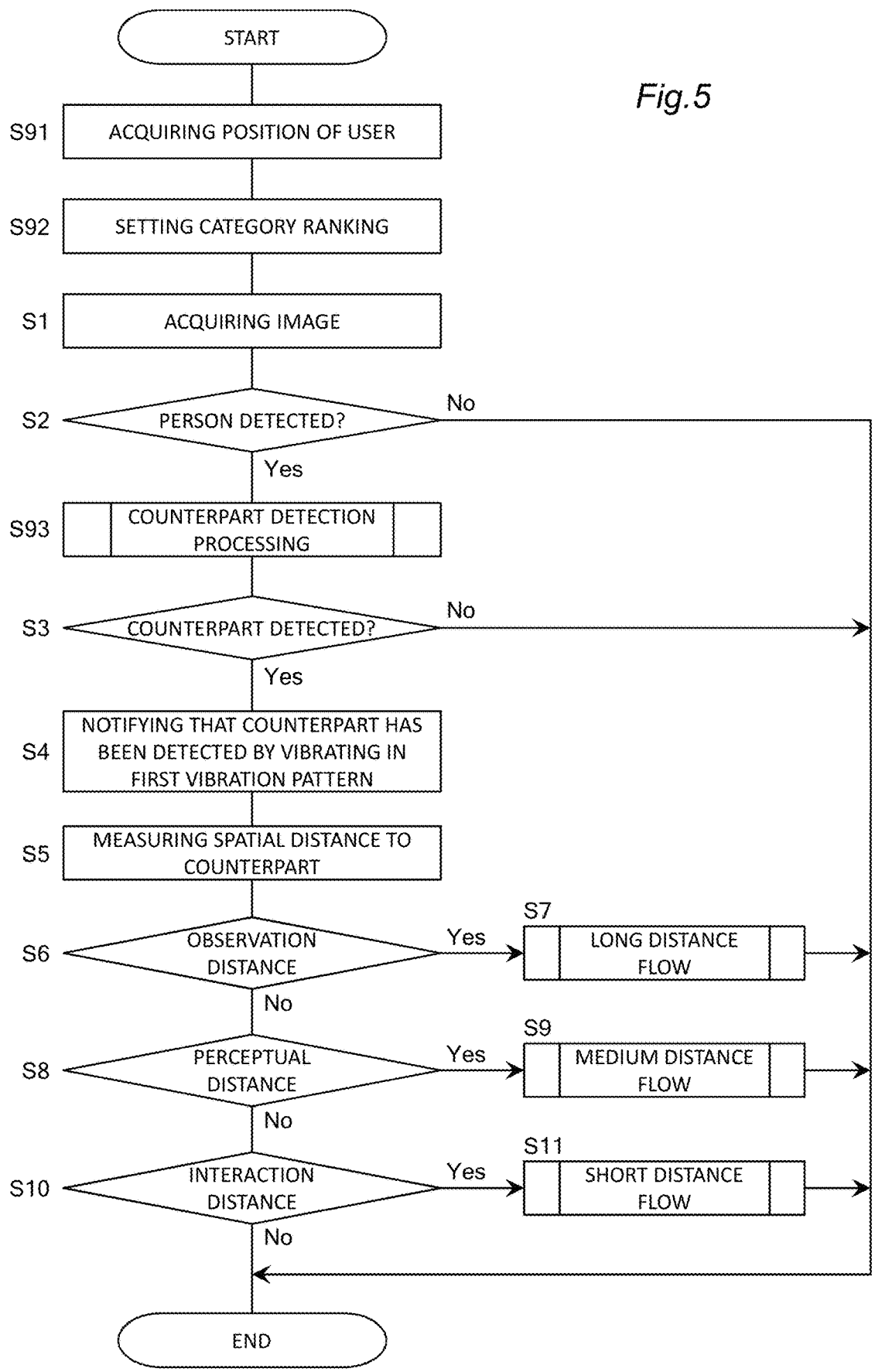
FIG. 5 is a flowchart illustrating an operation example of the communication support device according to the first embodiment of the present disclosure.

FIG. 5 is a flowchart illustrating the operation example of the communication support device 100 according to the present embodiment. The process illustrated in FIG. 5 is repeatedly executed by, for example, the controller 4.
(Step S91)

First, the position acquisition unit 48 acquires position information indicating a position of the communication support device 100 or the user 90, measured by the GPS receiver 7, from the GPS receiver 7 (S91).
(Step S92)

Next, the category ranking setting unit 49 sets category rankings in the category ranking information 50 based on the position information acquired by the position acquisition unit 48 in Step S91 (S92). For example, when the position acquired by the position acquisition unit 48 in Step S91 is located in a workplace area, the category ranking setting unit 49 updates the category ranking information 50 in the storage 5 from the initial values illustrated in FIG. 4A to current values illustrated in FIG. 4B. Here, the "workplace area" represents, for example, an area in a site of a workplace of the user 90 or an area around the workplace including a point separated from the site of the workplace of the user 90 by a predetermined distance.

Alternatively, when the position acquired by the position acquisition unit 48 in Step S91 is located in the workplace area, the category ranking setting unit 49 may update the category ranking information 50 in the storage 5 from rankings in the initial value field illustrated in FIG. 4C to values in the workplace area field. In addition, when the position acquired by the position acquisition unit 48 in Step S91 is located in a home area, the category ranking setting unit 49 may update the category ranking information 50 in the storage 5 to values in the home area field illustrated in FIG. 4C. Here, the "home area" represents, for example, an area in a site of the home of the user 90 or an area around the home of the user 90 including a point separated from the site of the home of the user 90 by a predetermined distance.

When the position acquired by the position acquisition unit 48 is not included in predetermined positions in Step S91, for example, the category ranking setting unit 49 may set the category ranking information 50 of the storage 5 to the initial values.
(Step S1)

Next, the image acquisition unit 41 acquires a captured image captured by the camera 3 (S1). For example, the camera 3 captures an image of a surrounding environment of the user 90 in a time-series manner to generate a plurality of pieces of captured image data. In this manner, the camera 3 may perform imaging at a constant frame rate. The camera 3 may capture a moving image. In Step S1, the image acquisition unit 41 may acquire a plurality of captured images. The image acquisition unit 41 may acquire a moving image formed of a plurality of frames, or may acquire a plurality of still images.
(Step S2)

Next, the counterpart detector 42 analyzes the captured image acquired by the image acquisition unit 41 to detect a person (S2). Here, detecting a person includes detecting a region in the captured image in which a person is presumed to be captured. If no person is detected in Step S2 (No in Step S2), the controller 4 ends the flow illustrated in FIG. 5.
(Step S93)

If a person is detected in Step S2 (Yes in Step S2), the counterpart detector 42 detects whether or not the person detected in Step S2 is a counterpart such as an acquaintance, based on the counterpart database 51 in which information about a face of the counterpart is stored (S93). What is executed in Step S3 is identity identification processing of identifying whether or not a face of the person detected in Step S2 matches or resembles the face of the counterpart.

For example, in Step S93, the counterpart detector 42 refers to the category ranking information 50 and the counterpart database 51 to detect the counterpart belonging to a category having a priority in the captured image in the order of the priority stored in the category ranking information 50. For example, in Step S93, the counterpart detector 42 searches for the person detected in Step S2 in the order of a category ranking from a counterpart belonging to a category having the highest category ranking to a counterpart belonging to a category having the lowest category ranking. The counterpart detector 42 detects a counterpart belonging to a category having the highest priority in the captured image. When the detection fails, the counterpart detector 42 detects a counterpart belonging to a category having a priority lower than the highest priority in order of priority.

Figure 6:
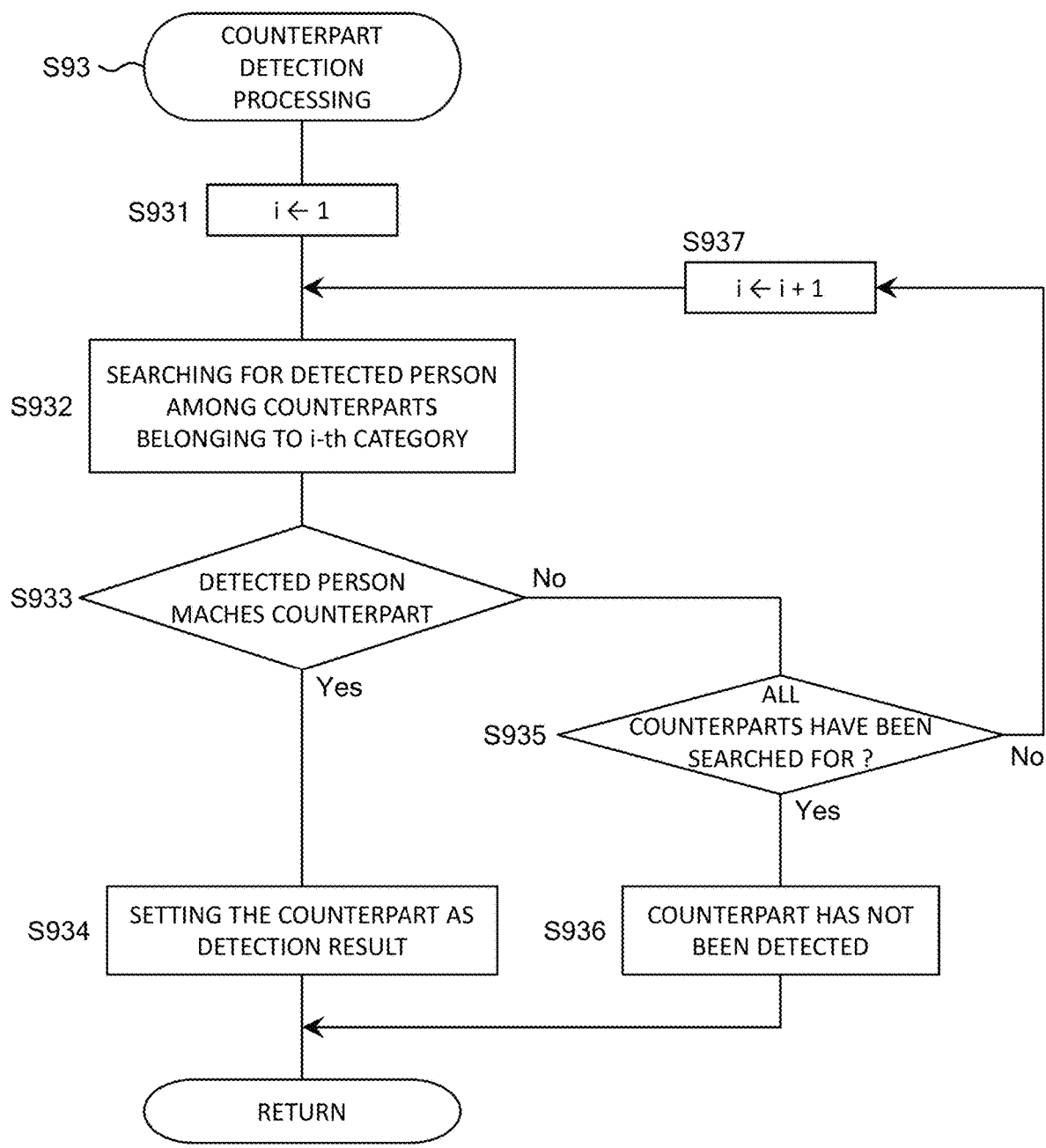
FIG. 6 is a flowchart illustrating an example of counterpart detection processing illustrated in FIG. 5.

FIG. 6 is a flowchart illustrating an example of counterpart detection processing illustrated in FIG. 5. First, the counterpart detector 42 sets an integer i to 1, which is an initial value (S931).

Next, the counterpart detector 42 searches for the person detected in Step S2 of FIG. 5 among counterparts belonging to the i-th category in the counterpart database 51 (S932). For example, when the integer i is 1, the counterpart detector 42 identifies whether the face of the person detected in Step S2 matches or resembles faces of counterparts (D and E in FIG. 3) belonging to the category (friend in FIG. 4A) having the first category ranking.

When the person detected in Step S2 is determined to match or resemble one of the counterparts belonging to the i-th category (Yes in Step S933), the counterpart detector 42 sets the counterpart as a detection result (S934). Thereafter, the processing proceeds to Step S3 in FIG. 5. In this case, it is unnecessary to search the counterpart database 51 for a counterpart other than the already searched counterpart, for example, a counterpart belonging to a category having a (i+1)th priority or lower, and thus, the communication support device 100 can end the search processing at an early stage.

When it is determined that the person detected in Step S2 does not match or resemble any counterpart belonging to the i-th category (No in Step S933), the counterpart detector 42 determines whether all counterparts in the counterpart database 51 have been searched for (S935).

If the search for all the counterparts in the counterpart database 51 has not yet been completed (No in Step S935), the counterpart detector 42 increments the integer i (S937) and returns to Step S932.

When it is determined that all the counterparts in the counterpart database 51 have been searched (Yes in Step S935), the counterpart detector 42 determines that the counterpart has not been detected (S936). In this case, it is assumed that data corresponding to the person detected in Step S2 is not stored in the counterpart database 51. Thereafter, the processing proceeds to Step S3 in FIG. 5.

(Step S3)

Returning to FIG. 5, if the counterpart has been detected in Step S93 (Yes in Step S3), the processing proceeds to Step S4. In the other case (No in Step S3), the controller 4 ends the flow illustrated in FIG. 5.

(Step S4)

When the counterpart is detected in Step S3, the vibration unit 2 notifies the user 90 that the counterpart has been detected by a vibration (S4). Specifically, the vibration unit 2 notifies the user 90 that the counterpart has been detected by vibrating in a first vibration pattern. In this manner, the vibration unit 2 performs feedback of the detection of the counterpart to the user 90 in order to alert the user 90. Details of the vibration pattern will be described later.

In Step S4, the feedback may be performed by the vibration in the first vibration pattern when the counterpart detected in Step S3 enters an observation distance, a perceptual distance, or an interaction distance, which will be described later. In this sense, predetermined distances such as the observation distance, the perceptual distance, and the interaction distance are referred to as feedback distances configured to perform the feedback. That is, the vibration unit 2 may vibrate in the first vibration pattern when the distance between the counterpart and the camera 3 detected by the distance measuring unit 45 is the observation distance, the perceptual distance, or the interaction distance in a case where the counterpart tracker 43 tracks the counterpart.

(Step S5)

Next, the distance measuring unit 45 detects a spatial distance between the camera 3 and the counterpart based on the information detected in Step S2, for example (S5). The spatial distance is an example of the "distance" of the present disclosure. Since the camera 3 is the wearable camera worn by the user 90, the camera mounted on the luggage of the user 90, or the like, it can be said that a spatial distance between the camera 3 and the counterpart is about the same as the spatial distance between the user 90 and the counterpart.

The spatial distance generally means a distance between two points and can vary depending on a path between these points. The spatial distance between the user 90 and the counterpart can be roughly classified into three categories, for example, the observation distance, the perceptual distance, and the interaction distance. In accordance with these spatial distances, a space around the user 90 can be roughly classified into an observation space, a perceptual space, and an interaction space. FIG. 7 is a schematic view for describing an example of the spatial distance.

The observation distance is, for example, a distance at which a person carefully observes an object or a counterpart in order to acquire information. For example, when another person is at the observation distance, the user 90 can observe the other person and identify whether or not the other person is an acquaintance and who the acquaintance is. The observation distance represents, for example, a distance longer than a predetermined second threshold. The observation distance corresponds to a case where the spatial distance between individuals is longer than, for example, 3.6 m.

The perceptual distance is, for example, a distance at which a motion and/or an emotion of another person is interpreted or perceived through the senses (for example, five senses, particularly, the visual and auditory senses). For example, when another person is at the perceptual distance, the user 90 can observe emotions such as enjoyment, anger, and sadness by observing a facial expression, a motion, and the like of the other person. In addition, for example, when another person is at the perceptual distance, the user 90 can recognize a motion such as whether the other person is looking at the user 90, is working by operating a telephone or a tablet, or is waving his/her hand at the user 90. The perceptual distance represents, for example, a distance longer than a predetermined first threshold and equal to or less than the second threshold. The perceptual distance corresponds to a case where the spatial distance between individuals is, for example, longer than 1.2 m and equal to or less than 3.6 m.

The interaction distance is, for example, a distance at which an interaction with another person, such as a conversation, is usually performed. The interaction distance represents, for example, a distance of the first threshold or less. The interaction distance corresponds to a case where the spatial distance between individuals is, for example, 1.2 m or less.

Here, the spatial distances that can be distinguished into the three categories of the observation distance, the perceptual distance, and the interaction distance has been described as an example. However, the concept of the spatial distance is not limited to these. For example, the spatial distance may be roughly classified into a public space, a social space, a personal space, and the like based on Proxemics (Hall, E. T., The hidden dimension, New York: Doubleday, 1966). In addition, the spatial distance may differ depending on the intimacy between persons, the culture to which a person belongs, a gender of a person, and the like.

(Steps S6 to S11)

Returning to FIG. 5, the controller 4 proceeds to Step S7 to execute a long distance flow if the spatial distance between the camera 3 and the counterpart is the observation distance as a result of the measurement in Step S5 (when Yes in Step S6). In the case of the perceptual space (Yes in Step S8), the controller 4 proceeds to Step S9 to execute a medium distance flow. In the case of the interaction space (Yes in Step S10), the controller 4 proceeds to Step S11 to execute a short distance flow. In this manner, the communication support device 100 executes different processes according to the spatial distance between the camera 3 and the counterpart at the timepoint when the counterpart is found in Step S3.

2-2-2. Long Distance Flow 2-2-2-1. Overall Flow

Figure 8A:
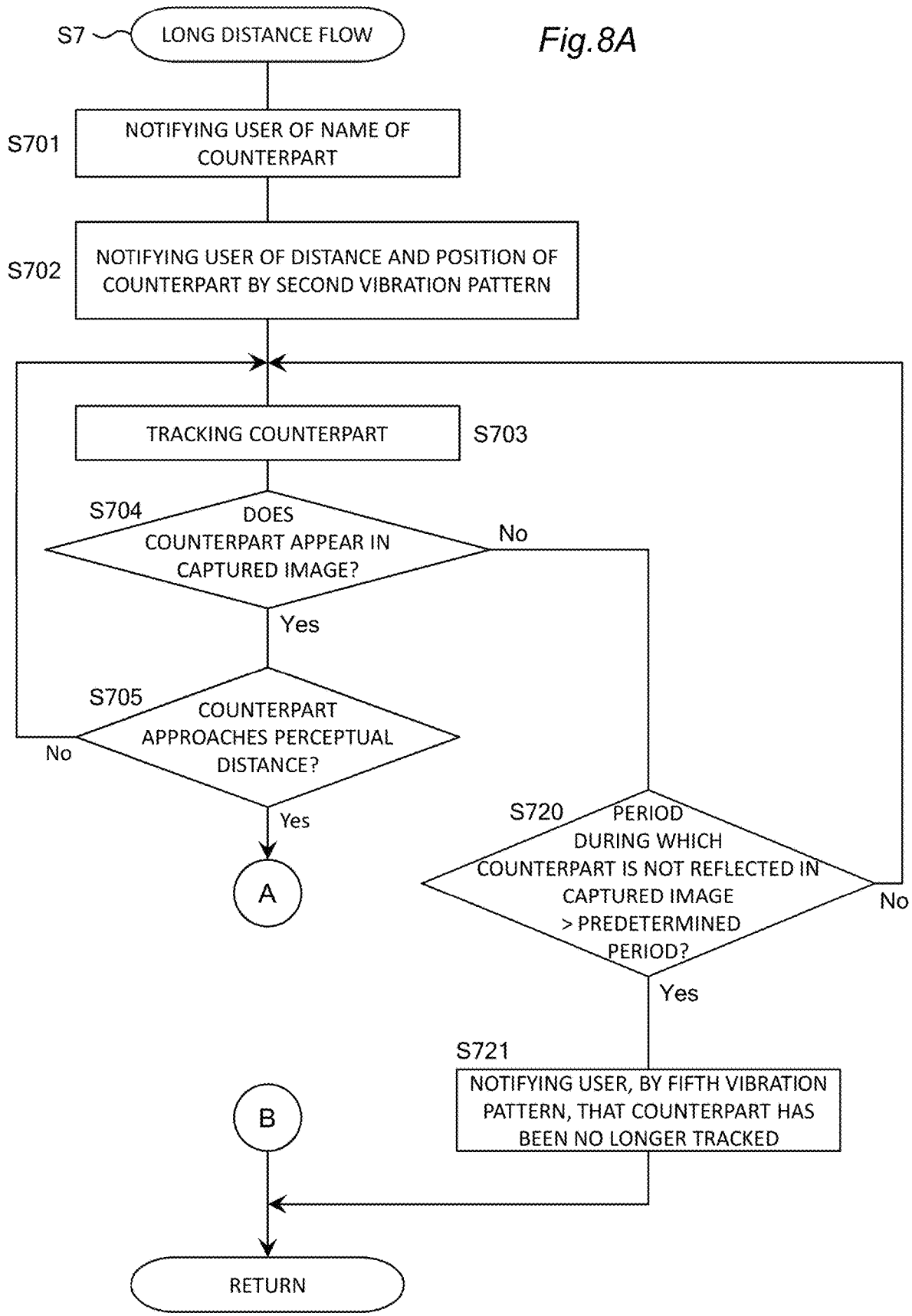
FIG. 8A is a flowchart illustrating a detailed flow of a long distance flow illustrated in FIG. 5.

FIG. 8A and FIG. 8B are flowcharts illustrating a detailed flow of the long distance flow (S7) illustrated in FIG. 5. FIG. 8A and FIG. 8B are connected by connector A and connector B. The flow illustrated in FIG. 8A and FIG. 8B may be executed in real time, that is, every time the image acquisition unit 41 acquires an image. Alternatively, the flow illustrated in FIG. 8A and FIG. 8B may be executed for captured images of a plurality of frames acquired by the image acquisition unit 41 for a few seconds to a few tens of seconds.

(Step S701)

First, the voice output unit 1 notifies the user 90 of a name of the counterpart detected in Step S3 by a voice (S701). As a result, the user 90 can know the name of the counterpart who is close to him/her and can identify who is close to him/her. The name of the counterpart is an example of the identification information for identifying the counterpart in the present disclosure.

(Step S702)

Next, the vibration unit 2 notifies the user 90 of a spatial distance to the counterpart and a position of the counterpart by a vibration (S702). Specifically, the vibration unit 2 notifies the user 90 of the position of the counterpart and that the counterpart is at the observation distance by vibrating in a second vibration pattern. Details of the vibration pattern will be described later. The spatial distance is the one measured by the distance measuring unit 45 in Step S5 of FIG. 5. The position of the counterpart is detected, for example, by the counterpart position detector 44. The position of the counterpart is determined, for example, by any direction of the right side, the front direction, or the left side where the counterpart exits with an optical axis of the camera 3 as a reference. Further, the position of the counterpart may be determined, for example, by any direction of the upper side and the lower side where the counterpart exists with the optical axis of the camera 3 as the reference. In other words, the position of the counterpart may represent an index that identifies any direction of up, down, left, right, and front where the counterpart exists as viewed from the user 90.

(Step S703)

Next, the counterpart tracker 43 tracks the counterpart detected in Step S3 of FIG. 5 (S703). Specifically, the counterpart tracker 43 tracks a counterpart in a current frame captured after a reference frame based on a position in an image of a counterpart detected or tracked in the reference frame. The counterpart can be tracked by, for example, saving the counterpart in the reference frame as a template in the storage 5 and applying a method such as known template matching using the template to search the current frame.

For example, the counterpart tracker 43 calculates a matching score indicating the certainty that the counterpart detected or tracked in the reference frame and the counterpart tracked in the current frame are the same counterpart. The matching score is, for example, a value in the range of 0 to 1, and a larger value means that there is a high possibility that the counterpart detected in the reference frame and the counterpart detected in the current frame are the same counterpart. When the matching score is a predetermined threshold or more, the counterpart tracker 43 determines that the counterpart detected in the reference frame and the counterpart detected in the current frame are the same counterpart, and considers that the tracking of the counterpart is successful.

(Step S704)

In the tracking processing, the counterpart tracker 43 determines whether or not the detected or tracked counterpart appears in the captured image (S704). For example, the counterpart tracker 43 determines whether or not the counterpart is reflected in the current frame. The process proceeds to Step S705 if it is determined that the counterpart is reflected in the captured image (Yes in Step S704), and proceeds to Step S720 if it is determined that the counterpart is not reflected (No in Step S704).

(Step S705)

The distance measuring unit 45 determines whether or not the counterpart has approached the perceptual distance (S705). Specifically, the distance measuring unit 45 determines whether or not the counterpart who was at the observation distance in the frame used in Step S5 of FIG. 5 is at the perceptual distance in a frame captured at the subsequent timing. For example, the distance measuring unit 45 determines that the counterpart has approached the perceptual distance when the distance between the camera 3 and the counterpart is 3.6 m. The process proceeds to Step S706 in FIG. 8B if the counterpart approaches the perceptual distance (Yes in Step S705), and returns to Step S703 if the counterpart has not approached the perceptual distance (No in Step S705). If the counterpart has not approached the perceptual distance, the controller 4 may end the processes of FIG. 8A and FIG. 5.

(Step S706)

In Step S706 illustrated in FIG. 8B, the expression determination unit 46 determines a facial expression of the counterpart based on the captured image (S706). Details of the facial expression determination processing step S706 will be described later.

(Step S707)

Next, the voice output unit 1 notifies the user 90 of facial expression information related to the facial expression determined by the expression determination unit 46 in Step S706 by a voice (S707). Here, the facial expression information may include not only information representing a human facial expression itself, but also information indicating whether a person wears a wearable object or a shield, such as a mask, an eye patch, eyeglasses, and sunglasses, on the face. For example, the voice output unit 1 notifies the user 90 of the facial expression information such as "smiling", "angry", "facial expression is unknown", and "wearing a mask". As a result, the user 90 can know the facial expression of the counterpart close to him/her, and can smoothly communicate according to the facial expression.

(Step S708)

Next, the vibration unit 2 notifies the user 90 of a spatial distance to the counterpart and a position of the counterpart by a vibration (S708). Specifically, the vibration unit 2 notifies the user 90 of the position of the counterpart and that the counterpart is at the perceptual distance by vibrating in a third vibration pattern. Details of the vibration pattern will be described later.

(Step S709)

Next, the motion determination unit 47 determines a motion of the counterpart based on the captured image (S709). Details of the motion determination processing step S709 will be described later.

(Step S710)

Next, the voice output unit 1 notifies the user 90 of motion information related to the motion determined by the motion determination unit 47 in Step S709 by a voice (S710). For example, the voice output unit 1 notifies the user 90 of the motion information such as "the counterpart is looking at you", "the counterpart is waving his/her hand", "the counterpart is talking on the phone", "the counterpart is coughing", and "the motion of the counterpart is unknown". As a result, the user 90 can know the motion of the counterpart, and can smoothly communicate according to the motion.

(Step S711)

Next, the distance measuring unit 45 determines whether or not the counterpart has approached the interaction distance (S711). Specifically, the distance measuring unit 45 determines whether or not the counterpart who was at the perceptual distance in the frame used in Step S705 of FIG. 8A is at the interaction distance in a frame captured at the subsequent timing. For example, the distance measuring unit 45 determines that the counterpart has approached the interaction distance when the distance between the camera 3 and the counterpart is 1.2 m. The process proceeds to Step S712 if the counterpart approaches the interaction distance (Yes in Step S711), and returns to Step S709 if the counterpart has not approached the interaction distance (No in Step S711). If the counterpart does not approach the interaction distance even after a lapse of a long period of time, the controller 4 may end the processes of FIG. 8B and FIG. 5.

(Step S712)

Next, the vibration unit 2 notifies the user 90 of a spatial distance to the counterpart and a position of the counterpart by a vibration (S712). Specifically, the vibration unit 2 notifies the user 90 of the position of the counterpart and that the counterpart is at the interaction distance by vibrating in a fourth vibration pattern. Details of the vibration pattern will be described later. As a result, the user 90 can know that the counterpart is at the interaction distance and can start communication with the counterpart.

(Step S713)

After Step S712, the controller 4 executes post-interaction processing, for example, after the user 90 finishes communicating with the counterpart, (S713). For example, the controller 4 controls the vibration unit 2 to notify that the counterpart has left the user 90 by a vibration. As a result, the user 90 can know that the counterpart has left, and can resume an action such as moving to a destination that has been taken before the communication with the counterpart.

(Step S720)

Returning to FIG. 8A, if it is determined in Step S704 that the counterpart is not reflected in the captured image, the controller 4 determines whether or not a period during which the counterpart is not reflected in the captured image is longer than a predetermined period. The predetermined period is, for example, one second to several minutes, for example, four seconds. Instead of the period, the number of frames may be set in advance. For example, the controller 4 may determine whether or not the counterpart is reflected in a predetermined number of consecutive frame images. The process proceeds to Step S721 if the period during which the counterpart is not reflected in the captured image is longer than the predetermined period (Yes in Step S720), and returns to Step S703 if the period is the predetermined period or less (No in Step S720).

(Step S721)

If the period during which the counterpart is not reflected in the captured image is longer than the predetermined period (Yes in Step S720), the vibration unit 2 notifies the user 90 that the counterpart has been no longer tracked by a vibration (S721). Specifically, the vibration unit 2 notifies the user 90 that the counterpart has been no longer tracked by vibrating in a fifth vibration pattern. Details of the vibration pattern will be described later. As a result, the user 90 can know that the counterpart has been no longer tracked or that the counterpart has left the periphery of the user 90. After Step S721, the components such as the controller 4 and the notification unit 10 may resume a navigation operation to a destination or the like, which is a normal operation performed before the detection of the counterpart, for the user 90.

2-2-2-2. Facial Expression Identification Processing

FIG. 9 is a flowchart illustrating a detailed flow of the facial expression determination processing step S706 illustrated in FIG. 8B.

(Step S7061)

First, the expression determination unit 46 analyzes the captured image and detects a face of the counterpart (S7061). Here, detecting the face includes detecting a region in the captured image in which a human is presumed to be captured.

(Step S7062)

If the face of the counterpart is detected (Yes in Step S7062), the process proceeds to Step S7063. If the face of the counterpart is not detected (No in Step S7062), the process proceeds to Step S7067.

(Step S7063)

If the face of the counterpart is detected (Yes in Step S7062), the expression determination unit 46 detects whether or not the counterpart is wearing a shield such as a mask, an eyepatch, eyeglasses, and sunglasses (S7063). There is a case where it is difficult to detect the face because the counterpart is wearing the shield, and thus, shield detection processing is adopted in the embodiment. For example, a technique disclosed in Japanese Patent Application Laid-Open No. 2018-151919 is applied to a method for detecting whether or not the counterpart is wearing the shield.

If it is detected in Step S7063 that the counterpart is wearing the shield (Yes in Step S7064), the expression determination unit 46 determines the face wearing the shield for the facial expression information related to the facial expression of the counterpart (S7068). The expression determination unit 46 may identify what the shield is. For example, in Step S7068, the expression determination unit 46 may determines the face wearing a mask for the facial expression information related to the facial expression of the counterpart.

If it is not detected in Step S7063 that the counterpart is wearing the shield (No in Step S7064), the expression determination unit 46 identifies the facial expression of the counterpart (S7065). For example, the expression determination unit 46 compares the expression database 52 storing information on human facial expressions with the face of the counterpart in the captured image and identifies the facial expression of the counterpart.

A known method may be used for the identification of the facial expression. For example, the expression determination unit 46 detects organs of a face (hereinafter, referred to as "facial organs") in the face of the counterpart. The facial organ is a collection of tissues including those having specific functions. For example, the facial organs include eyes, a nose, a mouth, and ears. The facial organs may include skin. The entire face may be included in the facial organs. The expression determination unit 46 identifies the facial expression based on information on the detected facial organs. For example, the expression determination unit 46 detects a distance between feature points of the face, such as eyes, eyebrows, and a mouth, or an edge of a facial surface as information representing a facial expression from the information on the facial organs.

For example, the expression determination unit 46 extracts a feature value related to a relative position and a shape of the facial organ based on position information of the facial organ. Examples of the feature value include a Haar-like feature value, a distance between feature points, and a Fourier descriptor. Next, the extracted feature value may be input to a facial expression discriminator configured to discriminate a facial expression to output a facial expression score (facial expression component value). Examples of the facial expression score include a smiling degree indicating the degree of smile, a happiness degree indicating the degree of happiness, and the like. The facial expression discriminator is constructed by learning a large number of face sample images by machine learning such as a neural network and a self-organizing map.

Identifying the facial expression includes discriminating a type of facial expression, that is, identifying a type of facial expression to be recognized by a word indicating an emotion. Here, the facial expression may be identified by a word indicating a single emotion or by a combination of words indicating emotions. When words indicating emotions are combined, the words that indicate the respective emotions may be weighted. For example, facial expressions are classified into seven types of "neutral", "enjoyment", "anger", "disgust", "surprise", "fear", and "sadness" based on Paul Ekman's facial expression analysis. A numerical score is output as a facial expression identification result such that a total of degrees of the seven types of facial expressions (also called facial expression likeness or facial expression degree) is one. A score of each facial expression is also called the facial expression component value.

The above facial expression discriminator is not necessarily one, and may be formed of seven discriminators that are in charge of the seven types of facial expressions described above.

As a method for presuming the facial expression, techniques exemplified in Japanese Patent Application Laid-Open No. 2019-111092, Japanese Patent Application Laid-Open No. 2016-149063, Japanese Patent Application Laid-Open No. 2014-206903, and the like may be applied.

(Step S7066)

The expression determination unit 46 determines the facial expression of the counterpart as the one identified in Step S7065 (S7066). For example, the expression determination unit 46 determines the facial expression of the counterpart as the facial expression of "enjoyment".

(Step S7067)

If the face of the counterpart is not detected in Step S7061 (No in Step S7062), the expression determination unit 46 determines the facial expression of the counterpart as "unknown" (S7067). The expression determination unit 46 may determines that the facial expression of the counterpart is "unknown because the face has not been detected". Here, a "case where the face of the counterpart has not been detected" includes a case where the face of the counterpart has not been detected in a captured image of one frame. In addition, the "case where the face of the counterpart has not been detected" may include a case where the face detection processing has been attempted on captured images of a plurality of frames, but the face of the counterpart has not been detected in any of the frames.

As described above, the facial expression information determined in the facial expression determination processing step S706 of FIG. 9 is notified to the user 90 in Step S707 illustrated in FIG. 8B. For example, the voice output unit 1 notifies the user 90 of the facial expression information such as "smiling", "angry", "facial expression is unknown", and "wearing a mask". As a result, the user 90 can know the facial expression of the counterpart close to him/her, and can smoothly communicate according to the facial expression. For example, the user 90 can choose not to talk to the counterpart when being notified of the facial expression information indicating that the counterpart is angry.

In addition, for example, when being notified of the facial expression information indicating that the counterpart is wearing the mask in a situation where an infectious disease is prevalent, the user 90 can chose to perform a motion such as moving away from the counterpart and to secure a social distance from the counterpart (social distancing). Alternatively, the user 90 can ask the counterpart about his/her physical condition, for example, when being notified of the facial expression information indicating that the counterpart is wearing the mask. When the counterpart is ill, in poor physical condition, and the like, the user 90 can choose to perform a motion to secure a social distance from the counterpart. In this manner, the user 90 can reduce a risk of infection from others such as the counterpart based on the information notified from the communication support device 100, for example, in the situation where infectious diseases are prevalent. In this manner, communicating with others while adjusting the distance to the others according to the situation is also included in smooth communication.

2-2-2-3. Motion Identification Processing

Figure 10:
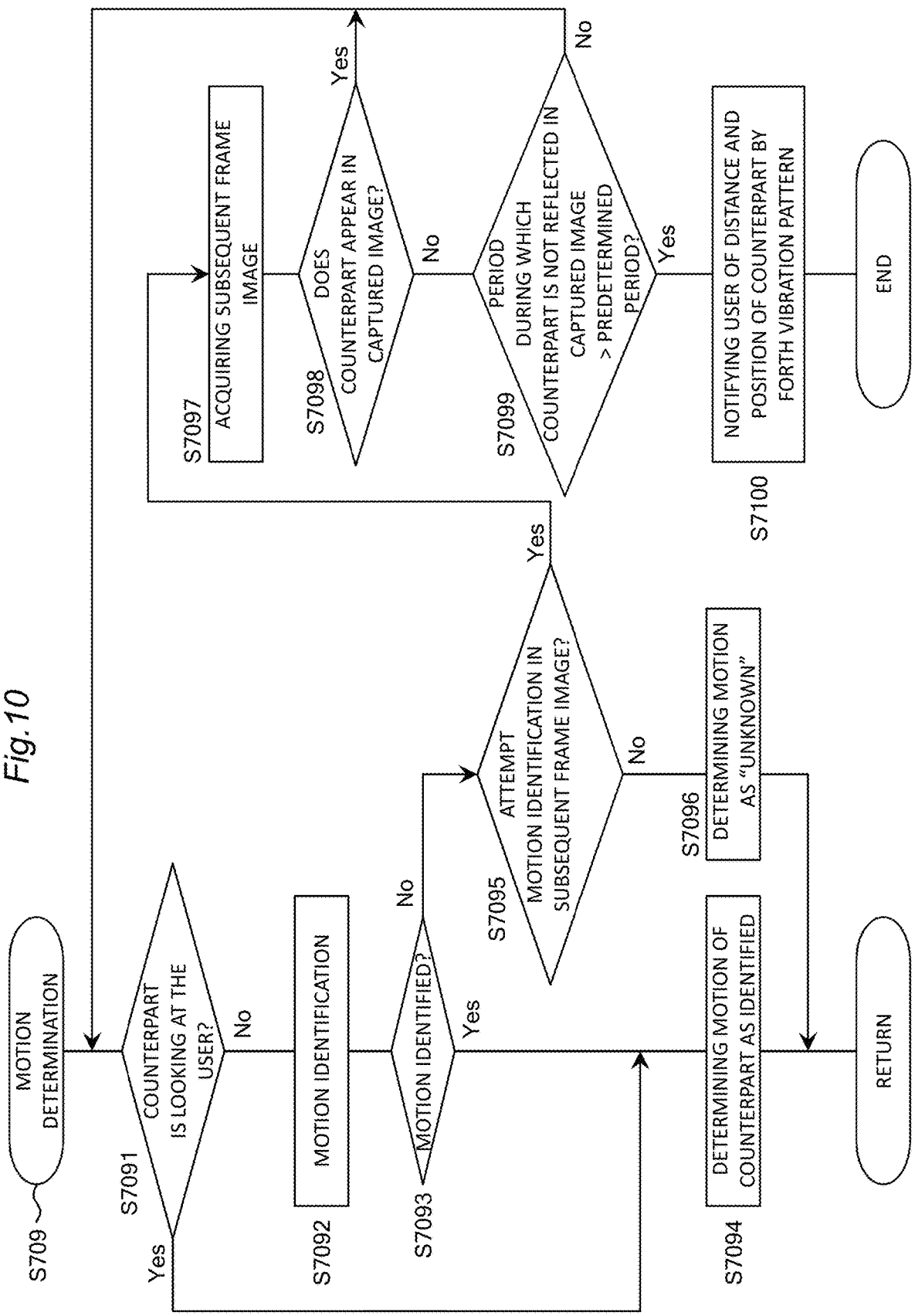
FIG. 10 is a flowchart illustrating a detailed flow of a motion determination processing step illustrated in FIG. 8B.

FIG. 10 is a flowchart illustrating a detailed flow of the motion determination processing step S709 illustrated in FIG. 8B.

(Step S7091)

First, the motion determination unit 47 detects whether or not the counterpart is looking at the user 90 (S7091). For example, the motion determination unit 47 detects whether or not a face of the counterpart is facing the camera 3. Since the camera 3 is the camera such as the wearable camera worn by the user 90 and the camera mounted on the luggage of the user 90, a case where the face of the counterpart is facing the camera 3 can be regarded as the same with a case where the counterpart is looking at the user 90. Alternatively, the motion determination unit 47 may detect irises or pupils of the counterpart to detect a line of sight of the counterpart based on positions of the detected irises or pupils. A case where a difference between a direction of the line of sight of the counterpart and a direction of the optical axis of the camera 3 is small can be regarded as the same with a case where the counterpart is looking at the user 90. If detecting that the counterpart is looking at the user 90 (Yes in S7091), the process proceeds to Step S7094.

(Steps S7092, S7093)

If the counterpart looking at the user 90 is not detected (No in S7091), the motion determination unit 47 identifies a motion of the counterpart (S7092). For example, the motion determination unit 47 compares the motion database 53 storing information on human motions with information on a motion such as a posture of the counterpart in the captured image, and identifies the motion of the counterpart. Examples of the motion of the counterpart include motions of the counterpart such as talking on the phone, reading a book, waving one's hand, running, walking, and coughing. Although whether or not the counterpart is looking at the user 90 is determined in Step S7091 in the above example, but the embodiment is not limited thereto. For example, the determination on whether or not the counterpart is looking at the user 90 may be included in the motion identification in Step S7092. The process proceeds to Step S7094 if the motion of the counterpart is identified (Yes in Step S7093), and proceeds to Step S7095 if the motion of the counterpart is not identified (No in Step S7093).

(Step S7094)

When the motion of the counterpart is identified (Yes in Step S7093), the motion determination unit 47 determines the motion of the counterpart as the one identified in Step S7092 (Step S7094). In addition, when it is detected in Step S7091 that the counterpart is looking at the user 90 (Yes in S7091), looking at the user 90 is identified for the motion of the counterpart in Step S7094. The determined motion is notified to the user 90 in Step S710 of FIG. 8B as described above.

(Step S7095)

If the motion of the counterpart is not identified in Step S7093, the motion determination unit 47 determines whether to attempt motion identification in another frame image captured at a timing subsequent to a timing when the frame image used in Step S7092 has been captured (S7095). Information on which period of a frame image the motion identification is attempted, or information on how many frame images the motion identification is attempted may be set in advance.

(Step S7096)

If it is determined in Step S7095 that no further motion identification is attempted (No in Step S7095), the motion determination unit 47 determines the motion of the counterpart as "unknown" (S7096). The identified motion is notified to the user 90 in Step S710 of FIG. 8B as described above.

(Step S7097)

The motion determination unit 47 acquires another frame image captured at a timing subsequent to a timing when the frame image used in Step S7092 has been captured (S7097).

(Step S7098)

Steps S7098 to S7100 are the same steps as Steps S704, S720, and S721 in FIG. 8A, respectively. In Step S7098, the motion determination unit 47 determines whether or not the counterpart is reflected in the frame image acquired in Step S7097 (S7098). The process return to Step S7091 if it is determined that the counterpart is reflected in the frame image (Yes in Step S7098), and proceeds to Step S7099 if it is determined that the counterpart is not reflected (No in Step S7098).

(Step S7099)

The controller 4 determines whether or not a period during which the counterpart is not reflected in the captured image is longer than a predetermined period (S7099). The process proceeds to Step S7100 if the period during which the counterpart is not reflected in the captured image is longer than the predetermined period (Yes in Step S7099), and returns to Step S7091 if the period is the predetermined period or less (No in Step S7099).

(Step S7100)

If the period during which the counterpart is not reflected in the captured image is longer than the predetermined period (Yes in Step S7099), the vibration unit 2 notifies the user 90 that the counterpart has been no longer tracked by a vibration (S7100). Specifically, the vibration unit 2 notifies the user 90 that the counterpart has been no longer tracked by vibrating in a fifth vibration pattern. As a result, the user 90 can know that the counterpart has been no longer tracked or that the counterpart has left the periphery of the user 90. After the notification in Step S7100, the controller 4 ends a series of processes illustrated in FIG. 5. The flow of FIG. 5 may be started repeatedly. The flow of FIG. 5 is started, for example, every predetermined cycle.

2-2-2-4. Post-Interaction Processing

Figure 11:
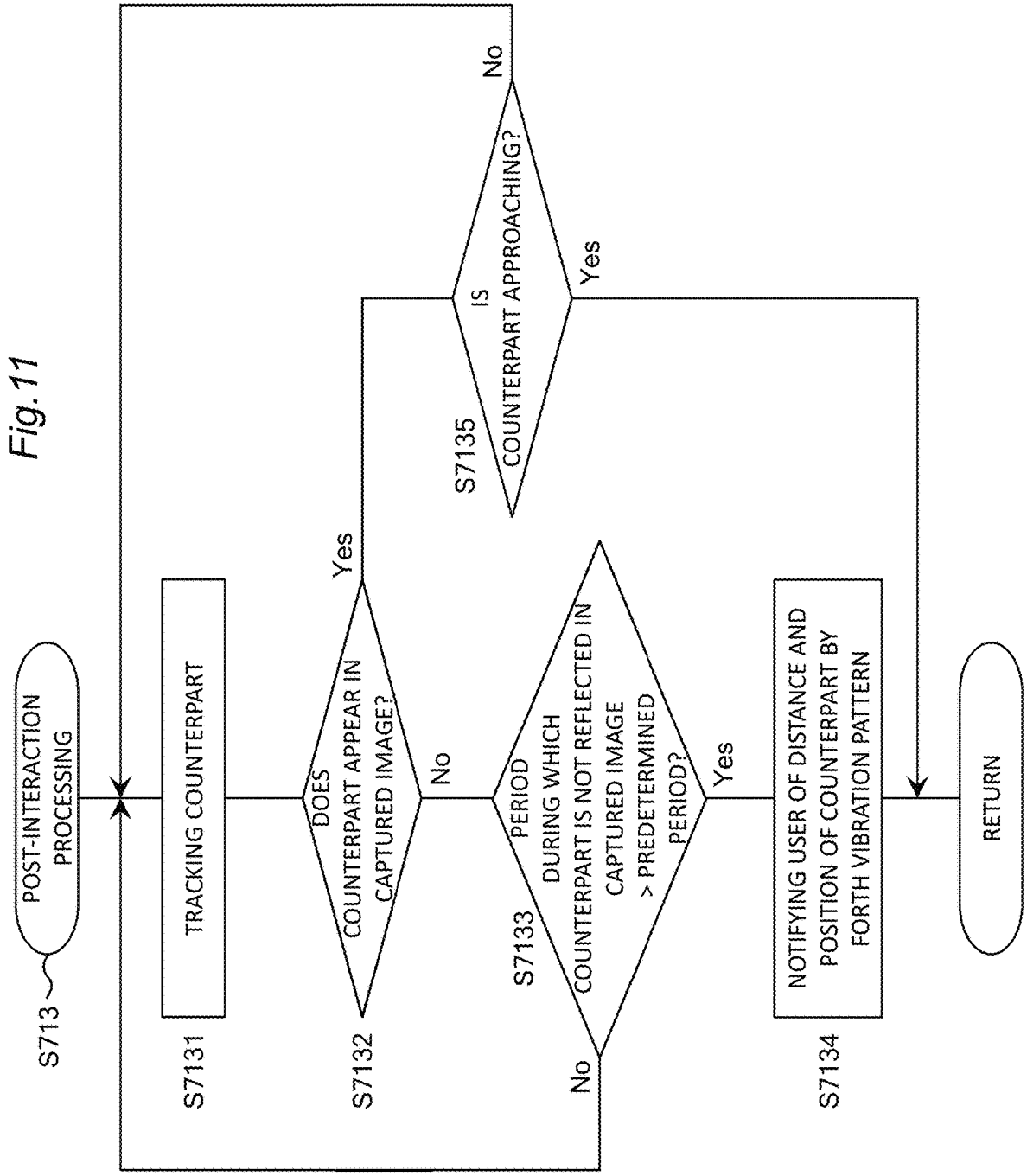
FIG. 11 is a flowchart illustrating a detailed flow of a post-interaction processing step illustrated in FIG. 8B.

FIG. 11 is a flowchart illustrating a detailed flow of the post-interaction processing step S713 illustrated in FIG. 8B.

(Step S7131)

First, the counterpart tracker 43 tracks the counterpart (S7131). In the tracking step S7131, the same processing as that in the tracking step S703 illustrated in FIG. 8A may be executed.

(Step S7132)

Next, the counterpart tracker 43 determines whether or not the detected or tracked counterpart appears in the captured image in the tracking processing (S7132). For example, the counterpart tracker 43 determines whether or not the counterpart is reflected in the current frame. The process proceeds to Step S7133 if it is determined that the counterpart is not reflected in the captured image (No in Step S7132), and proceeds to Step S7135 if it is determined that the counterpart is reflected (Yes in Step S7132).

(Step S7133)

The controller 4 determines whether or not a period during which the counterpart is not reflected in the captured image is longer than a predetermined period (S7133). The process proceeds to Step S7134 if the period during which the counterpart is not reflected in the captured image is longer than the predetermined period (Yes in Step S7133), and returns to Step S7131 if the period is the predetermined period or less (No in Step S7133).

(Step S7134)

If the period during which the counterpart is not reflected in the captured image is longer than the predetermined period (Yes in Step S7133), the vibration unit 2 notifies the user 90 that the counterpart has been no longer tracked by a vibration (S7134). Specifically, the vibration unit 2 notifies the user 90 that the counterpart has been no longer tracked by vibrating in a fifth vibration pattern. As a result, the user 90 can know that the counterpart has been no longer tracked or that the counterpart has left the periphery of the user 90. As a result, the user 90 can concentrate on a motion such as moving to a destination. Since the user 90 can concentrate on his/her own motion, the safety of the user 90 is also ensured. Step S7134 may be the same step as Step S721 illustrated in FIG. 8A.

(Step S7135)

If it is determined in Step S7132 that the counterpart is reflected in the captured image (Yes in Step S7132), the distance measuring unit 45 detects whether or not the counterpart is approaching (S7135). Specifically, the distance measuring unit 45 compares a distance between the camera 3 and the counterpart in two frame images captured at different timings, and detects whether or not the counterpart is approaching.

If detecting that the counterpart is approaching (Yes in Step S7135), the user 90 is likely to re-communicate with the counterpart. Therefore, the controller 4 may temporarily end the series of processes illustrated in FIG. 5 and start the process of FIG. 5 again. The flow of FIG. 5 is started, for example, every predetermined cycle. If detecting that the counterpart is not approaching (No in Step S7135), the controller 4 returns to Step S7131 and continues tracking.

2-2-2-5. Example of Long Distance Flow

Figure 12:
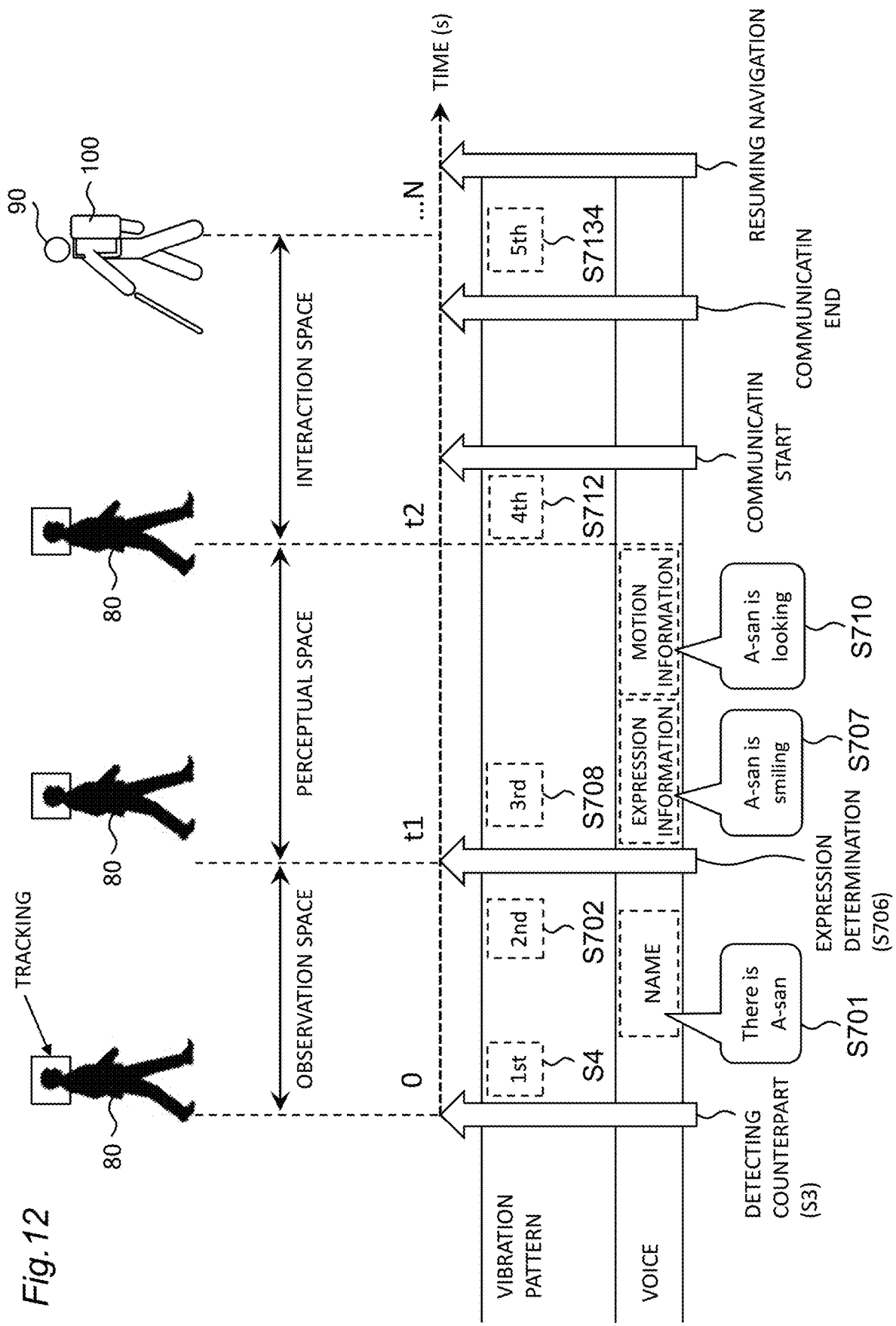
FIG. 12 is a schematic view illustrating an example of an operation including the long distance flow of the communication support device according to the first embodiment of the present disclosure.

FIG. 12 is a schematic view illustrating an example of an operation of the communication support device 100 when the detected spatial distance to the counterpart 80 is the observation distance (Yes in Step S6 of FIG. 5). When the communication support device 100 detects the counterpart 80 in the observation space, the communication support device 100 causes the vibration unit 2 to vibrate in the first pattern in order to alert the user 90. Next, the voice output unit 1 notifies the user 90 of the name of the counterpart 80 by the voice (S701), and the vibration unit 2 notifies the spatial distance to the counterpart 80 and the position of the counterpart 80 by vibrating in the second vibration pattern (S702).

Thereafter, when the counterpart 80 enters the perceptual space, the voice output unit 1 notifies the user 90 of the facial expression information of the counterpart 80 by the voice (S707), and the vibration unit 2 notifies the spatial distance to the counterpart and the position of the counterpart by vibrating in the third vibration pattern (S708). Further, the voice output unit 1 notifies the user 90 of the facial expression information of the counterpart 80 by the voice (S710).

Thereafter, when the counterpart 80 enters the interaction space, the vibration unit 2 notifies the spatial distance to the counterpart and the position of the counterpart by vibrating in the fourth vibration pattern (S712). As a result, the user 90 can know that the counterpart is at the interaction distance and can start communication with the counterpart. After the user 90 finishes communicating with the counterpart, for example, the vibration unit 2 notifies that the counterpart has left the user 90 by vibrating in the fifth vibration pattern (S7134). Thereafter, the components such as the controller 4 and the notification unit 10 may resume a navigation operation to a destination or the like, which is a normal operation performed before the detection of the counterpart, for the user 90.

2-2-3. Medium Distance Flow

Figure 13:
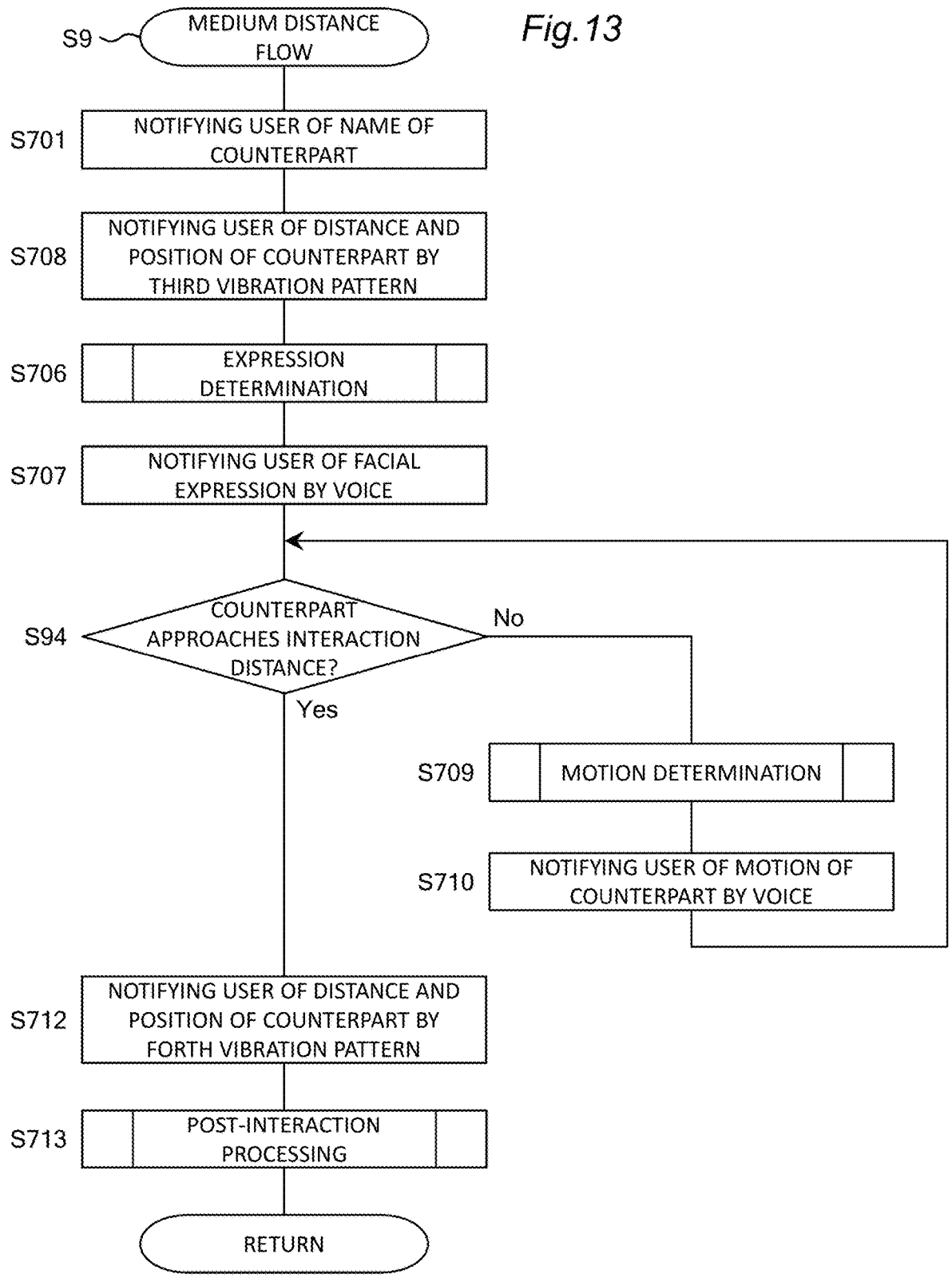
FIG. 13 is a flowchart illustrating a detailed flow of a medium distance flow illustrated in FIG. 5.

FIG. 13 is a flowchart illustrating a detailed flow of the medium distance flow (S9) illustrated in FIG. 5. In the medium distance flow, the same or similar steps as those described in the above-described long distance flow are denoted by the same reference signs. As such steps, the medium distance flow includes Steps S701, S706 to S710, S712, and S713. Duplicate descriptions are sometimes omitted for such steps.

In the medium distance flow, first, the voice output unit 1 notifies the user 90 of the name of the counterpart detected in Step S3 by the voice (S701). Next, the vibration unit 2 notifies the user 90 of a spatial distance to the counterpart and a position of the counterpart by a vibration (S708). Specifically, the vibration unit 2 notifies the user 90 of the position of the counterpart and that the counterpart is at the perceptual distance by vibrating in a third vibration pattern.

Next, the expression determination unit 46 determines the facial expression of the counterpart based on the captured image (S706). Next, the voice output unit 1 notifies the user 90 of facial expression information related to the facial expression determined by the expression determination unit 46 in Step S706 by a voice (S707). The facial expression determination processing step S706 may be executed before Step S701 of notifying the name of the counterpart.

Next, the distance measuring unit 45 determines whether or not the counterpart has approached the interaction distance (S94). Step S94 may be the same step as the above-described Step S711 illustrated in FIG. 8B. The process proceeds to Step S712 if it is determined that the counterpart has approached the interaction distance (Yes in Step S94), and proceeds to Step S709 if it is determined that the counterpart has not approached the interaction distance (No in Step S94).

If it is determined that the counterpart has approached the interaction distance (Yes in Step S94), the vibration unit 2 notifies the user 90 of the spatial distance to the counterpart and the position of the counterpart by a vibration (S712). Specifically, the vibration unit 2 notifies the user 90 of the position of the counterpart and that the counterpart is at the interaction distance by vibrating in a fourth vibration pattern.

Next, the controller 4 executes the post-interaction processing, for example, after the user 90 finishes communicating with the counterpart (S713).

If it is determined in Step S94 that the counterpart has not approached the interaction distance (No in Step S94), the motion determination unit 47 determines the motion of the counterpart based on the captured image (S709). Next, the voice output unit 1 notifies the user 90 of motion information related to the motion determined by the motion determination unit 47 in Step S709 by a voice (S710).

Figure 14:
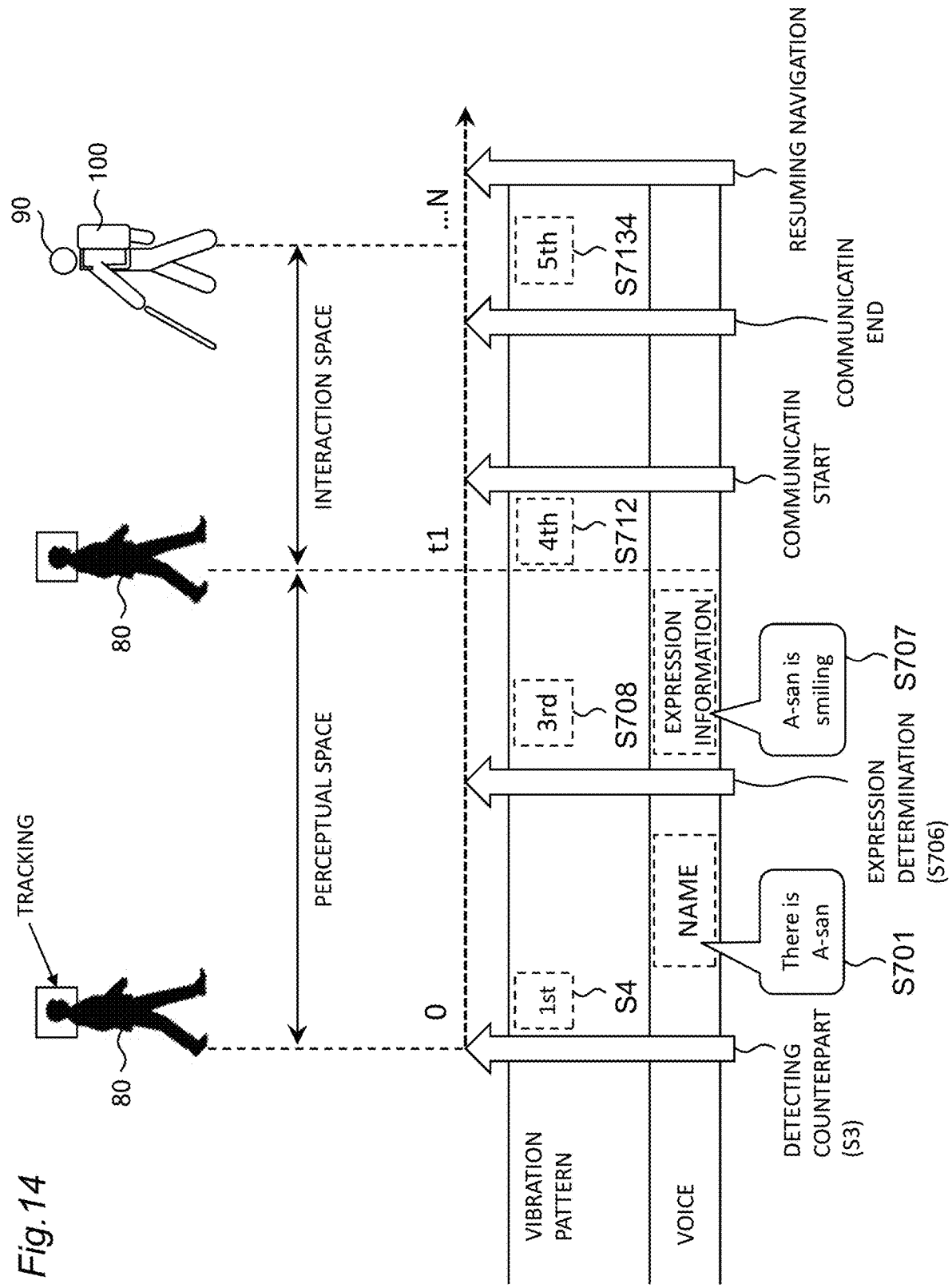
FIG. 14 is a schematic view illustrating an example of an operation including the medium distance flow of the communication support device according to the first embodiment of the present disclosure.

FIG. 14 is a schematic view illustrating an example of an operation of the communication support device 100 when the detected spatial distance to the counterpart 80 is the perceptual distance (Yes in Step S8 of FIG. 5). When compared with the schematic view in the case of the observation distance illustrated in FIG. 12, Step S710 of notifying the motion of the counterpart by the voice is particularly omitted in FIG. 14. If Step S710 of notifying the motion of the counterpart by the voice is executed when the counterpart approaches the interaction distance, the user is likely to pass and fail to smoothly communicate with the counterpart during the notification. Therefore, Step S710 is omitted in the medium distance flow depending on the distance to the counterpart. However, in the medium distance flow, the controller 4 additionally executes the motion determination processing step S709 as described above when, for example, the counterpart stays at the perceptual distance without approaching the interaction distance. As a result, the communication support device 100 also provides the user 90 with the motion information depending on a situation, even when the counterpart has been detected for the first time at the perceptual distance. The user 90 can smoothly communicate with the counterpart by receiving sufficient information according to the situation.

2-2-4. Short Distance Flow

Figure 15:
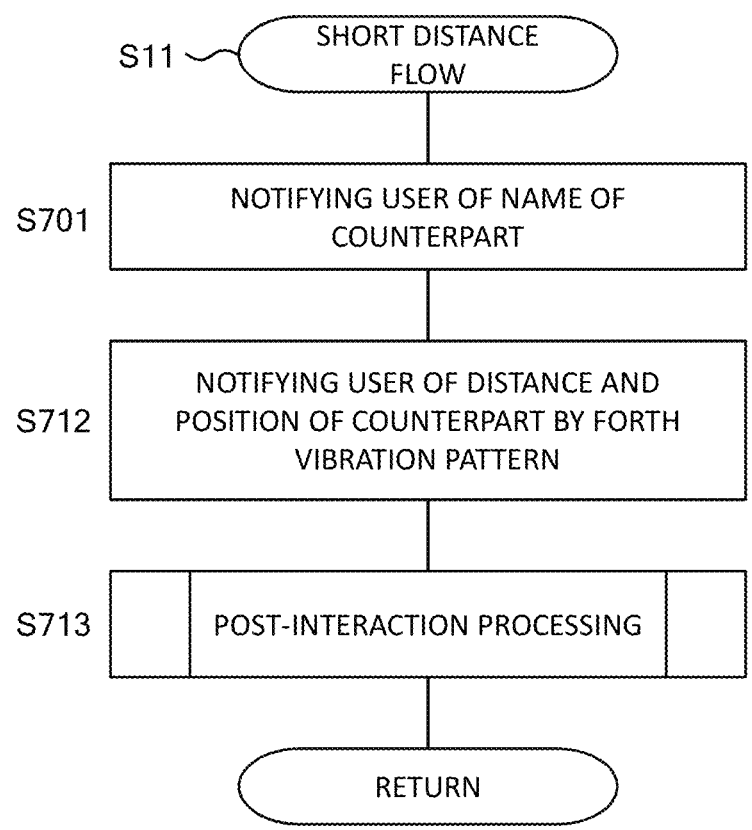
FIG. 15 is a flowchart illustrating a detailed flow of a short distance flow illustrated in FIG. 5.

FIG. 15 is a flowchart illustrating a detailed flow of the short distance flow (S11) illustrated in FIG. 5. In the short distance flow, the same or similar steps as those described in the above-described long distance flow are denoted by the same reference signs. As such steps, the short distance flow includes Steps S701, S712, and S713. Duplicate descriptions are sometimes omitted for such steps.

In the short distance flow, first, the voice output unit 1 notifies the user 90 of the name of the counterpart detected in Step S3 by the voice (S701). Next, the vibration unit 2 notifies the user 90 of a spatial distance to the counterpart and a position of the counterpart by a vibration (S712). Specifically, the vibration unit 2 notifies the user 90 of the position of the counterpart and that the counterpart is at the interaction distance by vibrating in a fourth vibration pattern. Next, the controller 4 executes the post-interaction processing, for example, after the user 90 finishes communicating with the counterpart (S713).

Figure 16:
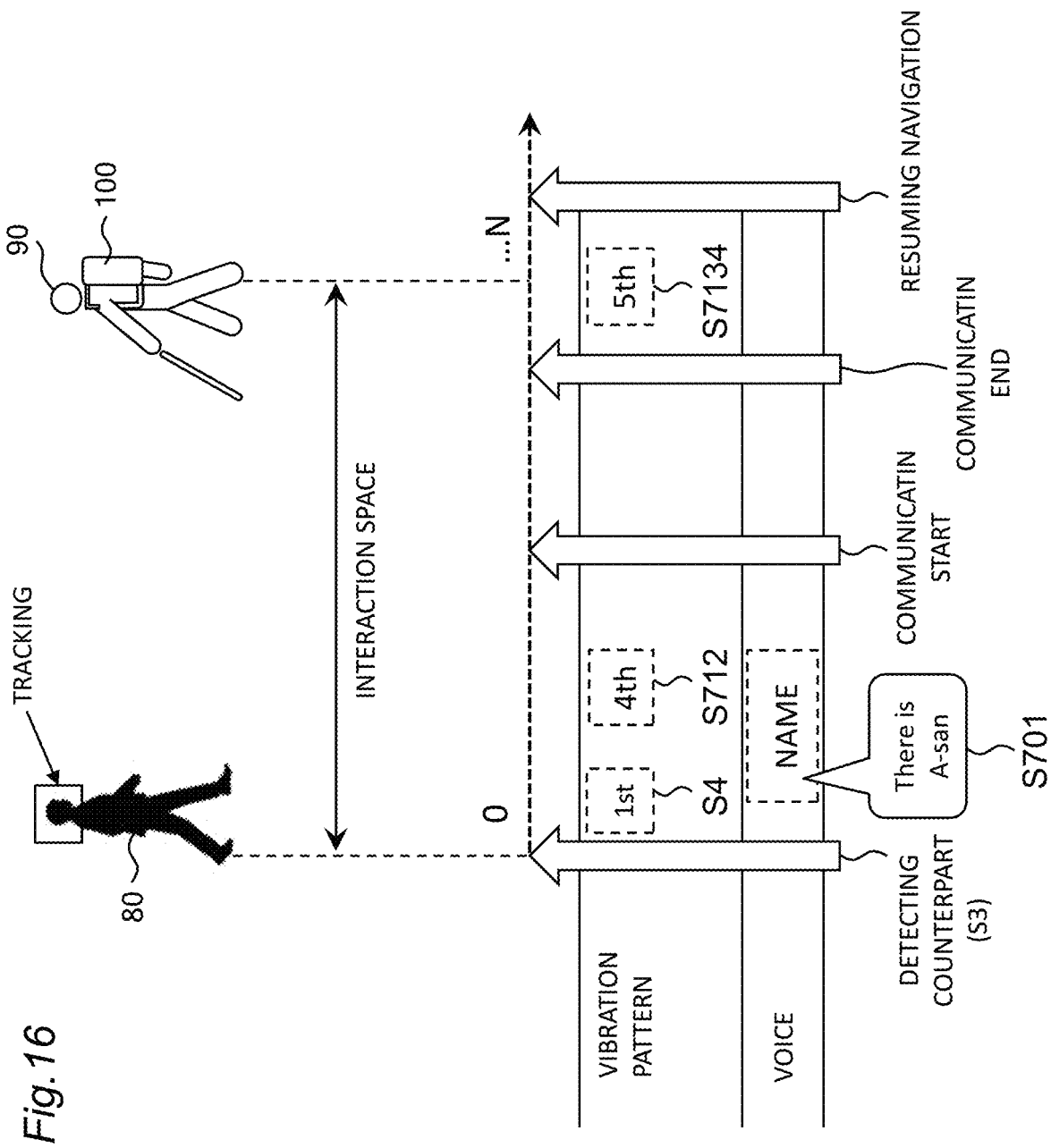
FIG. 16 is a schematic view illustrating an example of an operation including the short distance flow of the communication support device according to the first embodiment of the present disclosure.

FIG. 16 is a schematic view illustrating an example of an operation of the communication support device 100 when the detected spatial distance to the counterpart 80 is the interaction distance (Yes in Step S10 of FIG. 5). When compared with the schematic view in the case of the perceptual distance illustrated in FIG. 14, particularly, Step S707 of notifying the facial expression of the counterpart by the voice is further omitted in FIG. 16. When the counterpart is found at a short distance such as the interaction distance, the user 90 can immediately start communicating with the counterpart. In such a case, there is no time to notify the user 90 of a lot of information such as the facial expression and the motion of the counterpart by the voice or vibration, and smooth communication is normally difficult if the user 90 is notified of such information. Therefore, in the short distance flow, the communication support device 100 notifies the user 90 of only the minimum information such as the name, the distance, and the position of the counterpart to achieve the smooth communication between the user 90 and the counterpart.

2-3. Vibration Pattern

2-3-1. Configuration of Vibration Unit

Figure 17:
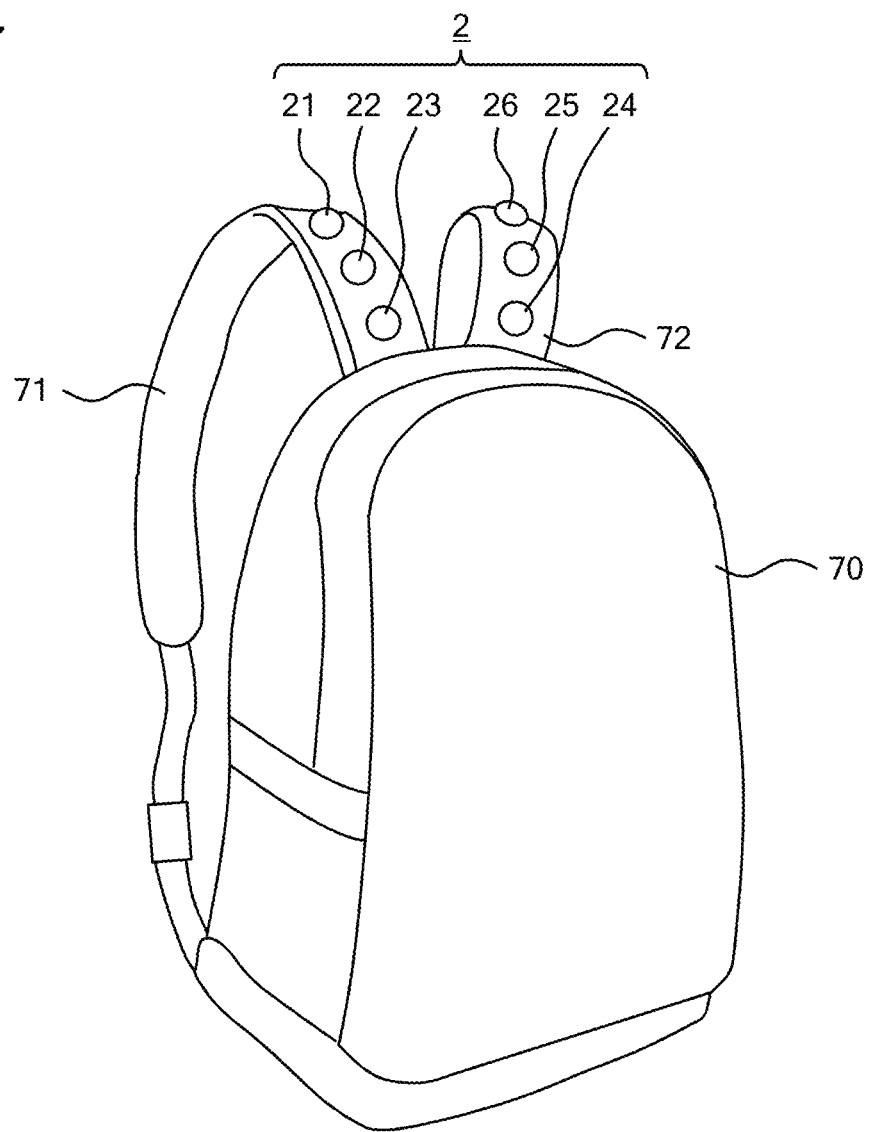
FIG. 17 is a view illustrating a configuration example of a vibration unit.

The vibration unit 2 and the vibration patterns of the vibration unit 2 will be described with reference to FIG. 17. FIG. 17 is a view illustrating a configuration example of the vibration unit 2. The vibration unit 2 is attached to, for example, shoulder straps of a rucksack 70. The vibration unit 2 includes two or more vibrating elements each of which vibrates according to a control signal from the controller 4. In the example of FIG. 17, the vibration unit 2 includes first to sixth vibrating elements 21 to 26 which are regularly arranged. The first to third vibrating elements 21 to 23 are attached to a left shoulder strap 71, and the fourth to sixth vibrating elements 24 to 26 are attached to a right shoulder strap 72. The first to third vibrating elements 21 to 23 are aligned in a direction in which the left shoulder strap 71 extends. The fourth to sixth vibrating elements 24 to 26 are aligned in a direction in which the right shoulder strap 72 extends. The first to third vibrating elements 21 to 23 are examples of a "left vibrating element" of the present disclosure. The fourth to sixth vibrating elements 24 to 26 are aligned in a direction in which the right shoulder strap 72 extends. The first to third vibrating elements 21 to 23 are examples of a "right vibrating element" of the present disclosure.

2-3-2. First Vibration Pattern

In the above example, the first vibration pattern is a vibration pattern for notifying the user 90 that the counterpart has been detected as described in Step S4 of FIG. 5. The first vibration pattern has a function of alerting the user 90.

In the first vibration pattern, the controller 4 causes the first to sixth vibrating elements 21 to 26 of the vibration unit 2 to sequentially vibrate. That is, in the first vibration pattern, the controller 4 performs control such that the first vibrating element 21, the second vibrating element 22, the third vibrating element 23, the fourth vibrating element 24, the fifth vibrating element 25, and the sixth vibrating element 26 vibrate in this order. When the rucksack 70 in a state of being carried by the user 90 is viewed from above, the first to sixth vibrating elements 21 to 26 vibrate in order counterclockwise in the first vibration pattern. The user 90 can know that the counterpart is nearby by feeling the counterclockwise vibration. This counterclockwise vibration may be executed once or a plurality of times.

2-3-3. Second Vibration Pattern

In the above example, the second vibration pattern is a vibration pattern for notifying the user 90 of the position of the counterpart and that the counterpart is at the observation distance as described in Step S702 of FIG. 8A.

For example, each of the vibrating elements 21 to 26 of the vibration unit 2 can vibrate with three levels of vibration intensities of weak, medium, and strong. In the second vibration pattern, each of the vibrating elements 21 to 26 of the vibration unit 2 notifies the user 90 that the counterpart is at the observation distance, for example, by a weak vibration. Alternatively, the controller 4 may notify the user 90 of the position of the counterpart by changing vibrating elements such as frequencies and waveforms of the vibrations of the vibrating elements 21 to 26.

Regarding the position of the counterpart, for example, when the counterpart is on the left side, the vibration unit 2 notifies the user 90 that the counterpart is on the left side by causing only the first to third vibrating elements 21 to 23 attached to the left shoulder strap 71 to vibrate. In addition, for example, when the counterpart is on the right side, the vibration unit 2 notifies the user 90 that the counterpart is on the right side by causing only the fourth to sixth vibrating elements 24 to 26 attached to the right shoulder strap 72 to vibrate. In addition, for example, the vibration unit 2 causes all of the first to sixth vibrating elements 21 to 26 to vibrate when the counterpart is in the front direction.

In this manner, the vibration unit 2 can notify the user 90 of both the spatial distance to the counterpart and the position of the counterpart substantially at the same time by controlling the intensity of the vibration and the position of the vibration.

2-3-4. Third Vibration Pattern

In the above example, the third vibration pattern is a vibration pattern for notifying the user 90 of the position of the counterpart and that the counterpart is at the perceptual distance as described in Step S708 of FIG. 8B and FIG. 13. In the third vibration pattern, each of the vibrating elements 21 to 26 of the vibration unit 2 notifies the user 90 that the counterpart is at the perceptual distance, for example, by vibrating with a medium intensity. Since the third vibration pattern is the same as the above-described second vibration pattern except that the vibration intensity is different, the duplicate description will be omitted.

2-3-5. Fourth Vibration Pattern

In the above example, the fourth vibration pattern is a vibration pattern for notifying the user 90 of the position of the counterpart and that the counterpart is at the interaction distance as described in Step S712 of FIG. 8B and FIG. 13. In the fourth vibration pattern, each of the vibrating elements 21 to 26 of the vibration unit 2 notifies the user 90 that the counterpart is at the interaction distance, for example, by vibrating with a strong intensity. Since the fourth vibration pattern is the same as the above-described second vibration pattern and third vibration pattern except that the vibration intensity is different, the duplicate description will be omitted.

2-3-6. Fifth Vibration Pattern

In the above example, the fifth vibration pattern is a vibration pattern for notifying the user 90 that it is difficult to track the counterpart that has been tracked as described in Step S721 of FIG. 8A and Step S7134 of FIG. 11. The fifth vibration pattern enables the user 90 to know that the counterpart has been no longer tracked or that the counterpart has left the periphery of the user 90.

In the fifth vibration pattern, the controller 4 causes the first to sixth vibrating elements 21 to 26 of the vibration unit 2 to sequentially vibrate in a different order from the first vibration pattern. For example, in the fifth vibration pattern, the controller 4 performs control such that the sixth vibrating element 26, the fifth vibrating element 25, the fourth vibrating element 24, the third vibrating element 23, the second vibrating element 22, and the first vibrating element 21 vibrate in this order. When the rucksack 70 in the state of being carried by the user 90 is viewed from above, the first to sixth vibrating elements 21 to 26 vibrate in order clockwise in the fifth vibration pattern. The user 90 can know that the counterpart has been no longer tracked or that the counterpart has left the periphery of the user 90 by feeling the clockwise vibration. This clockwise vibration may be executed once or a plurality of times.

In addition, the first to fifth vibration patterns are not limited to those described above as long as the user 90 can distinguish the first to fifth vibration patterns from each other. For example, the first to fifth vibration patterns may be patterns that vibrate in different vibration cycles.

2-3-7. Modification

In the example of FIG. 17, the example in which the first to sixth vibrating elements 21 to 26 of the vibration unit 2 are attached to the shoulder straps 71 and 72 of the rucksack 70 has been described. However, the present disclosure is not limited thereto as long as the user 90 can distinguish the first to fifth vibration patterns from each other. For example, the first to sixth vibrating elements 21 to 26 of the vibration unit 2 may be attached to a belt, a wristband, a wristwatch, a hat, or the like of the user 90. The first to sixth vibrating elements 21 to 26 of the vibration unit 2 may be incorporated in smart wear. Here, the smart wear is, for example, a wearable device in which a sensor, an output device, and the like is provided on a wearable material such as clothing. The first to sixth vibrating elements 21 to 26 of the vibration unit 2 are incorporated into smart textiles and materials constituting the smart wear.

2-4. Operation and Effect

As described above, the communication support device 100 according to the embodiment includes the position acquisition unit 48, the camera 3, the storage 5, the category ranking setting unit 49, the counterpart detector 42, and the notification unit 10. The position acquisition unit 48 acquires position information indicating a position of a user 90. The camera 3 captures an image of a surrounding environment of the user 90 to acquire a captured image. The storage 5 stores the counterpart database 51. In the counterpart database 51, an image of a counterpart and a category indicating a property of the counterpart are associated with the counterpart. The category ranking setting unit 49 sets a priority to the category according to the position information acquired by the position acquisition unit 48. The counterpart detector 42 detects a counterpart belonging to the category in the captured image in order of the priority set by the category ranking setting unit 49. The notification unit 10 notifies the user 90 of information regarding the counterpart detected by the counterpart detector 42.

In this manner, the counterpart detector 42 detects the counterpart belonging to the category in the captured image in order of the priority set by the category ranking setting unit 49. For example, the communication support device 100 searches the counterpart database for one matching or resembling the person appearing in the captured image in descending order of category ranking. As a result, the communication support device 100 can reduce the time required to detect the counterpart. If the counterpart can be quickly detected, the notification unit 10 can quickly notify the user 90 of information. Therefore, the user 90 can quickly obtain information regarding the counterpart 80 present in the periphery, and can smoothly or naturally communicate with the counterpart.

The communication support device 100 may include the distance measuring unit 45, the expression determination unit 46, and the motion determination unit 47. The distance measuring unit 45 measures the distance between the counterpart and the camera 3 based on the captured image. The expression determination unit 46 determines the facial expression of the counterpart based on the captured image. The motion determination unit 47 determines the motion of the counterpart based on the captured image. When the distance between the counterpart and the camera 3 measured by the distance measuring unit 45 is the interaction distance of the first threshold or less, the notification unit 10 notifies the user 90 of the identification information for identifying the counterpart by, for example, the voice. When the distance between the counterpart and the camera 3 is longer than the first threshold, the notification unit 10 notifies the user 90 of the identification information and at least one of the facial expression information determined by the expression determination unit 46 and the motion information determined by the motion determination unit 47, by the voice.

With this configuration, the communication support device 100 can notify at least one of the facial expression information and the motion information is notified, and as much information in addition to the identification information, and notifies as much information as possible to the user 90 when the distance between the counterpart and the camera 3 is longer than the first threshold. On the other hand, when the distance between the counterpart and the camera 3 is small, the user 90 is likely to pass the counterpart during reading if the entire information detected by the communication support device 100 is read. In this case, it is difficult for the user 90 to communicate smoothly with the counterpart. Therefore, the communication support device 100 notifies the user 90 of only the identification information when the distance between the counterpart and the camera 3 is the first threshold or less. In this manner, the communication support device 100 omits the information to be notified when the distance is short, and supports the user 90 to smoothly communicate with the counterpart.

When the distance measured by the distance measuring unit 45 is the perceptual distance longer than the first threshold and equal to or less than the second threshold, the notification unit 10 may notify the user 90 of the identification information and one of the facial expression information and the motion information. When the distance measured by the distance measuring unit 45 is the observation distance longer than the second threshold, the notification unit 10 may notify the user 90 of the facial expression information, the motion information, and the identification information.

In this manner, the user 90 can quickly find out pertinent information about the counterpart and can communicate smoothly with the counterpart by gradually omitting the information to be notified to the user 90 as the distance between the counterpart and the camera 3 becomes shorter.

When the distance between the counterpart and the camera 3 measured by the distance measuring unit 45 at a timepoint when detection has been performed by the counterpart detector 42, is the perceptual distance, the notification unit 10 may notify the user 90 of the identification information by the voice, and then, notify the user 90 of one of the facial expression information and the motion information by the voice. Thereafter, when the distance between the counterpart and the camera 3 measured by the distance measuring unit 45 is the perceptual distance, the notification unit 10 may notify the user 90 of the other of the facial expression information and the motion information by the voice.

With this configuration, even in the case where the counterpart has been detected for the first time at the perceptual distance, the user 90 can know both the facial expression information and the motion information when the counterpart stays at the perceptual distance without approaching the interaction distance. In this manner, the user 90 can smoothly communicate with the counterpart by receiving the appropriate amount of information according to the situation.

The notification unit 10 may include the vibration unit 2 that notifies the user 90 of a detection result obtained by the distance measuring unit 45 by the vibration. The vibration unit 2 may change at least one of the vibration pattern and the magnitude according to the distance between the counterpart and the camera 3 detected by the distance measuring unit 45.

The vibration unit 2 enables the communication support device 100 to notify the user 90 of a part or whole of the detection result in a shorter time as compared with the voice notification. In addition, when the voice notification and the vibration notification are combined, the communication support device 100 can convey a large amount of information to the user 90 in a shorter time as compared with a case where only the voice notification is used.

The camera 3 may acquire a plurality of captured images by capturing an image of the surrounding environment of the user 90 in a time-series manner. In this case, the communication support device 100 may further include the counterpart tracker 43 that tracks the counterpart detected by the counterpart detector 42 in the plurality of captured images. The vibration unit 2 may include two or more vibrating elements that can vibrate. In this case, the vibration unit 2 may cause the respective vibrating elements to sequentially vibrate in a predetermined order when the distance between the counterpart and the camera 3 detected by the distance measuring unit 45 is a predetermined feedback distance in the case where the counterpart tracker 43 tracks the counterpart. In the case where it is difficult for the counterpart tracker 43 to track the counterpart that has been tracked, the vibration unit 2 may cause the respective vibrating elements to sequentially vibrate in an order different from the predetermined order.

When vibration patterns in which the two or more vibrating elements vibrate in different orders are provided, the communication support device 100 can notify the user 90 of various types of information by vibrations. The user 90 can recognize that the distance to the counterpart is the feedback distance and a difference between the possibility of communication and the difficulty in tracking the counterpart that has been tracking based on a difference in the vibration pattern.

The vibrating elements may be three or more vibrating elements which are regularly arranged. The vibration unit 2 may cause the respective vibrating elements to sequentially vibrate in an arranged order when the distance between the counterpart and the camera 3 detected by the distance measuring unit 45 is the feedback distance in the case where the counterpart tracker 43 tracks the counterpart. When it is difficult for the counterpart tracker 43 to track the counterpart that has been tracked, the respective vibrating elements may be made to sequentially vibrate in a reverse order of the arranged order.

When vibration patterns in which the three or more vibrating elements vibrate in different orders are provided, the user 90 can more clearly distinguish and recognize a difference in the information notified by the vibration as compared with the case where there are only two vibrating elements or less.

The communication support device 100 may further include the counterpart position detector 44 that detects the position of the counterpart with respect to the camera 3 based on the captured image. The vibrating elements may include a right vibrating element and a left vibrating element. The vibration unit 2 may cause the right vibrating element to vibrate when the position of the counterpart with respect to the camera 3 detected by the counterpart position detector 44 is the right side of the optical axis of the camera 3, and may cause the left vibrating element to vibrate when the position of the counterpart is the left side of the optical axis of the camera 3.

With this configuration, the communication support device 100 can more clearly notify the user 90 of the relative position of the counterpart by the vibration.

3. Second Embodiment

Figure 18:
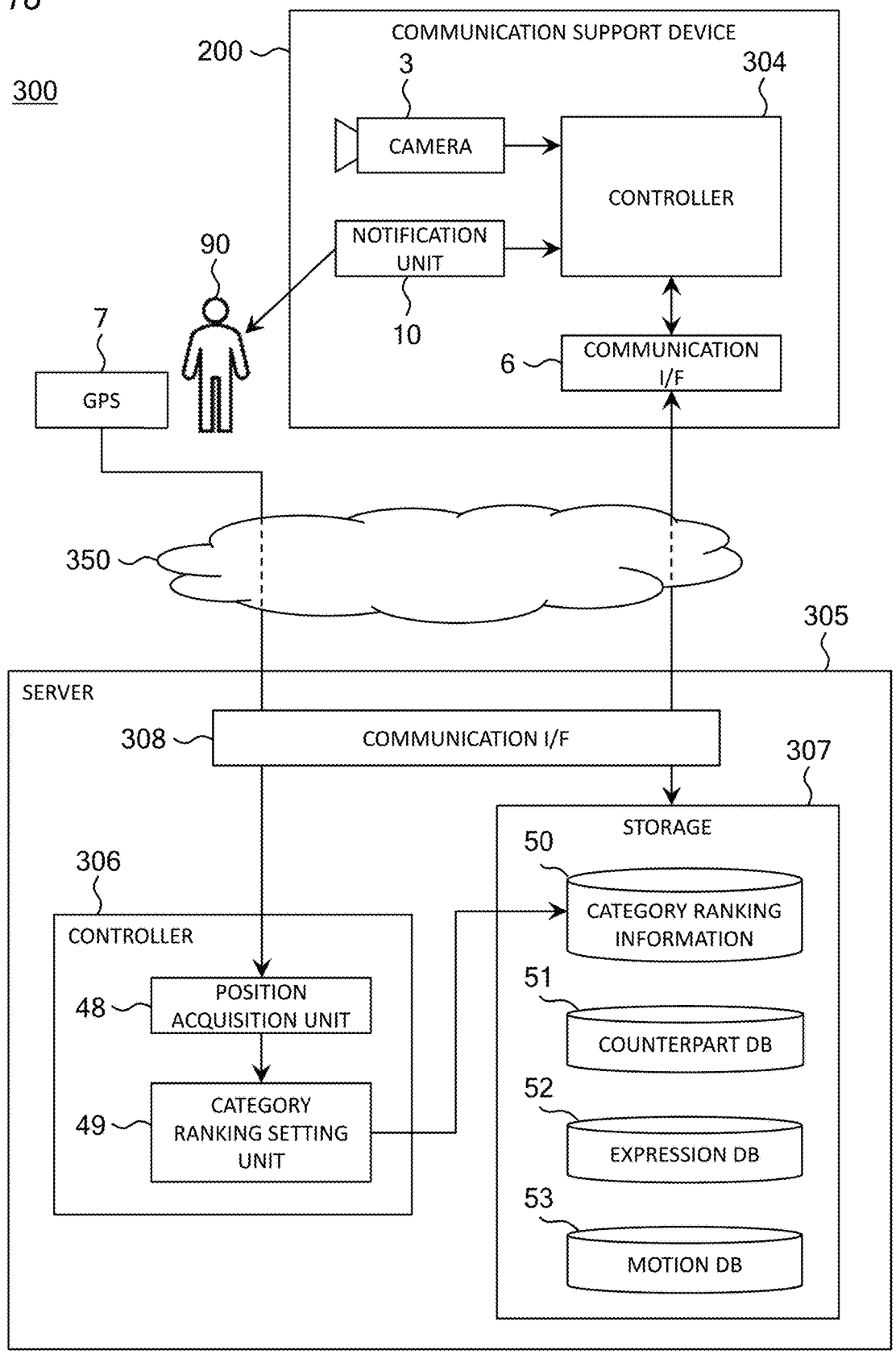
FIG. 18 is a block diagram illustrating a configuration example of a communication support system according to a second embodiment of the present disclosure.

FIG. 18 is a block diagram illustrating a configuration example of a communication support system 300 according to a second embodiment of the present disclosure. The communication support system 300 includes a communication support device 200, a server 305, and a GPS receiver 7. The GPS receiver 7 is carried by the user 90. As described in the first embodiment, the GPS receiver 7 may be mounted in an information processing device such as a mobile phone and a smartphone carried by the user 90.

The server 305 is an information processing device including a controller 306, a storage 307, and a communication interface 308. The controller 306 of the server 305 is an information processing device similar to the controller 4. The communication interface 308 is an example of a "transmission unit" and a "reception unit" of the present disclosure, and is, for example, an interface circuit similar to the communication interface 6.

The communication support device 200 includes the camera 3, the controller 304, the communication interface 6, and the notification unit 10. As compared with the communication support device 100 of FIG. 2, the communication support device 200 of FIG. 18 does not include the category ranking information 50, the counterpart database 51, the expression database 52, and the motion database 53 in the storage. Instead, the category ranking information 50, the counterpart database 51, the expression database 52, and the motion database 53 are stored in the storage 307 of the server 305 that is connected to the communication support device 200 via a network 350 so as to enable communication.

The controller 304 of the communication support device 200 includes the image acquisition unit 41, the counterpart detector 42, the counterpart tracker 43, the counterpart position detector 44, the distance measuring unit 45, the expression determination unit 46, and the motion determination unit 47. As compared with the controller 4 in FIG. 2, the controller 304 in FIG. 18 does not include the position acquisition unit 48 and the category ranking setting unit 49. Instead, the controller 306 of the server 305 includes the position acquisition unit 48 and the category ranking setting unit 49.

The position acquisition unit 48 acquires position information indicating a position of the user 90 from the GPS receiver 7 via the network 350 and the communication interface 308.

Although an example in which the notification unit 10 is included in the communication support device 200 has been described in the above example, the present disclosure is not limited thereto. For example, the notification unit 10 may be mounted on an information processing device such as a mobile phone and a smartphone carried by the user 90.

As described above, the server 305 according to the present embodiment includes the position acquisition unit 48, the counterpart database 51, the category ranking setting unit 49, and the communication interface 308. The position acquisition unit 48 of the controller 306 acquires position information indicating a position of the user 90 from, for example, the GPS receiver 7. The controller 306 transmits information in the counterpart database 51 and information indicating a priority set by the category ranking setting unit 49 to the communication support device 200 via the communication interface 308 and the network 350.

The communication support device 200 receives the information in the counterpart database 51 and the information indicating the priority set by the category ranking setting unit 49 from the server 305. The communication support device 200 includes the camera 3, the counterpart detector 42, and the notification unit 10. The camera 3 captures an image of the surrounding environment of the user 90 to acquire the captured image.

The counterpart detector 42 detects a counterpart belonging to a category in the captured image in the order of the priority set by the category ranking setting unit 49 of the server 305. The notification unit 10 notifies the user 90 of information regarding the counterpart detected by the counterpart detector 42.

The communication support device 200 enables the user 90 to quickly obtain the information regarding the surrounding counterpart, which is similar to the first embodiment. Therefore, the user 90 can smoothly or naturally communicate with the counterpart. Furthermore, the server 305 stores a database that may be large in capacity, and executes processing by the category ranking setting unit 49. As a result, the communication support device 200 can extract required data via the network 350 only when necessary, and can reduce a processing load applied to the controller 304. In addition, it is unnecessary to mount a processor having a high processing capability or a large-capacity storage device on the communication support device 200, and thus, it is possible to realize cost reduction and size reduction.

4. Modification

Although the embodiment of the present disclosure has been described in detail as above, the above description is merely an example of the present disclosure in all respects. Various improvements and modifications can be made without departing from the scope of the present disclosure. For example, the following changes can be made. Note that the same reference signs will be used for the same components as those in the above embodiment hereinafter, and the same points as those in the above embodiment will be omitted as appropriate. The following modifications can be combined as appropriate. In addition, modifications of the first embodiment of the present disclosure will be mainly described hereinafter, but these modifications are also applicable to the second embodiment of the present disclosure.

4-1. First Modification

In FIG. 5 of the first embodiment, the processing example in which Step S91 of acquiring the position of the user 90 and Step S92 of setting the category ranking are executed before the image acquisition step S1 has been described. However, the embodiments of the present disclosure are not limited thereto. For example, Steps S91 and S92 may be executed as processing different from the processing after image acquisition step S1 in FIG. 5. For example, Step S91 of acquiring the position of the user 90 and Step S92 of setting the category ranking may be processed in parallel with the processing after the image acquisition step S1 in FIG. 5.

In addition, the step of setting the category ranking is not necessarily executed in a case where the user 90 is not moving including walking, running, and the like. As a result, the processing in the case where the user 90 is not moving can be omitted, and a load on the controller 4 can be reduced.

Figure 19:
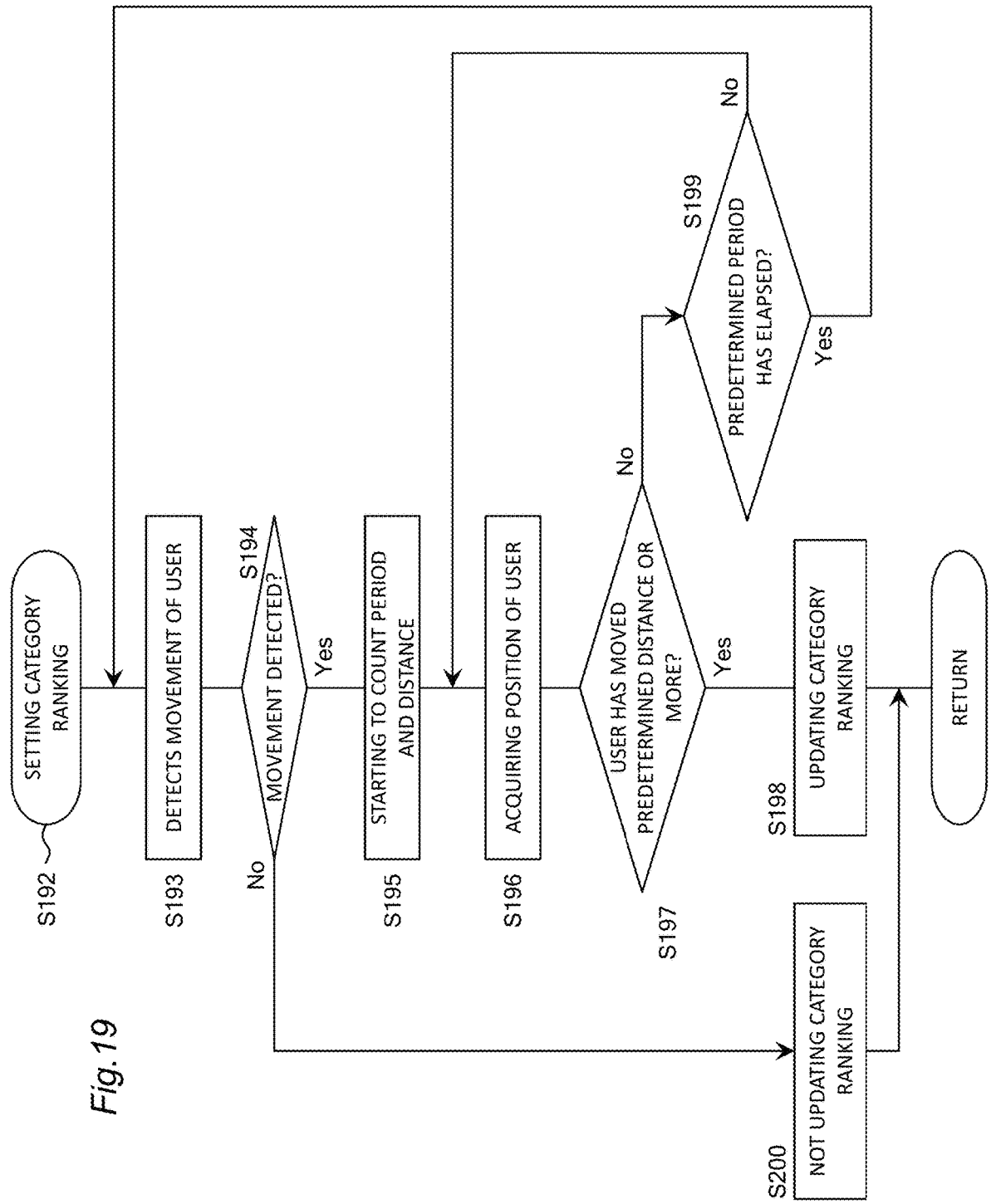
FIG. 19 is a flowchart illustrating a modification of category ranking setting processing.

FIG. 19 is a flowchart illustrating category ranking setting processing S192 which is a first modification of the above step of setting the category ranking. Step S91 (see FIG. 5) of acquiring the position of the user 90 and the category ranking setting processing S192 may be repeatedly executed at a predetermined cycle by the controller 4, for example.

First, the category ranking setting unit 49 detects movement of the user 90 (S193). For example, the communication support device 100 may further include a sensor, such as an accelerometer and a speedometer, in order to detect the movement of the user 90. Alternatively, the movement of the user 90 may be detected by a sensor, such as an accelerometer and a speedometer, mounted on a portable device such as a smartphone of the user 90. In this case, a detection result is transmitted from the portable device such as the smartphone of the user 90 to the communication support device 100 via a network or by wireless communication, for example.

When the movement of the user 90 is not detected (No in Step S194), the category ranking setting unit 49 does not update the category ranking information 50 in the storage 5 (S200).

When the movement of the user 90 is detected (Yes in Step S194), the category ranking setting unit 49 starts measurement of a period from the time and a distance from the position (S195). For example, the category ranking setting unit 49 resets the period and the distance, and starts to count a period and a distance. Regarding the distance, the category ranking setting unit 49 may store the position in the storage 5 as a predetermined position.

Next, the position acquisition unit 48 acquires position information indicating a position of the communication support device 100 or the user 90 measured by the GPS receiver 7 from the GPS receiver 7 and transmits the position information to the category ranking setting unit 49 (S196). Step S196 may be the same step as Step S91 illustrated in FIG. 5.

Next, the category ranking setting unit 49 determines whether the communication support device 100 or the user 90 has moved a predetermined distance or more from the predetermined position in Step S195 (S197). Here, the predetermined distance is, for example, a distance of 100 m or more, for example, a distance of 500 m, 1 km, 2 km, 5 km, or 10 km.

When it is determined that the communication support device 100 or the user 90 has moved the predetermined distance or more (Yes in Step S197), the category ranking setting unit 49 updates the category ranking information 50 in the storage 5 (S198).

When it is not determined in Step S197 that the communication support device 100 or the user 90 has moved the predetermined distance or more (No in Step S197), the category ranking setting unit 49 determines whether a predetermined period has elapsed from the time in Step S195 (S199). Here, the predetermined period is, for example, a period required for the user 90 to move 1 km on foot. For example, the predetermined period is a period of 3 minutes or more, for example, a period of 5 minutes, 10 minutes, 12 minutes, 15 minutes, 30 minutes, or the like.

When it is determined that the predetermined period has elapsed (Yes in Step S199), the processing returns to Step S193. When it is not determined that the predetermined period has elapsed (No in Step S199), the processing returns to Step S196.

In this manner, it is possible to reduce the load on the controller 4 including the category ranking setting unit 49 by omitting the processing in the case where the user 90 is not moving. As a result, for example, the controller 4 can allocate the processing capability to other processing such as the processing after the image acquisition step S1 in FIG. 5 and improve the processing speed. Therefore, the controller 4 can execute communication support processing at the processing speed closer to real time and support the realization of smooth communication by the user 90.

4-2. Second Modification

In the first embodiment, the communication support device 100 carried by the user 90 has been described. However, the present disclosure is not limited thereto. For example, the communication support device 100 may be mounted on a navigation robot that supports movement of the user 90 by performing an operation such as guiding the user 90 to a destination. Such a navigation robot can support smooth communication of the user 90 in addition to the movement support of the user 90. Such a navigation robot may be a self-propelled robot that supports the movement of the user 90 by, for example, self-propelling and leading the user 90 to a place where the user 90 wants to go.

Figure 20:
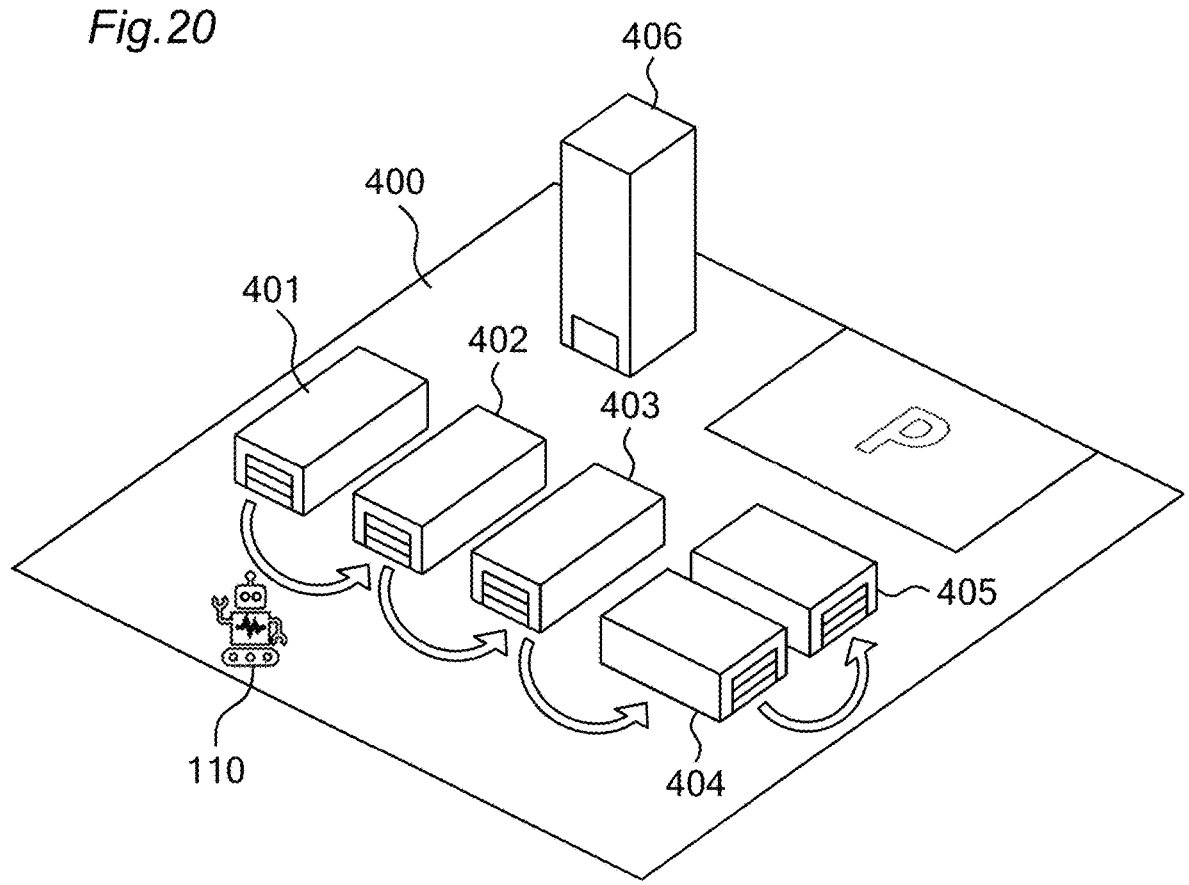
FIG. 20 is a schematic view for describing an operation example of a communication robot according to a modification of the embodiment of the present disclosure.

Alternatively, the communication support devices according to the embodiments of the present disclosure may be applied to a case where the user is a robot. FIG. 20 is a schematic view for describing an operation example of a communication robot 110 according to a second modification. The communication support device 100 or 200 according to the above embodiments is mounted on the communication robot 110.

The communication robot 110 travels, for example, in a site of a factory 400 and performs work while communicating with other people, other robots, and the like. For example, the communication robot 110 is a transport robot that autonomously enters a building 401, receives a part manufactured in the building 401 from a worker, and delivers the part to a worker in a building 402. Alternatively, the communication robot 110 may be a working robot that moves in the building 401 to a building 406 and executes manufacturing work performed in the buildings 401 to 406. The communication robot 110 may be a cooperative robot that performs such work in cooperation with a person or a working robot. In addition, the communication robot 110 may be a guide robot that guides a visitor to the factory 400.

Since the communication robot 110 moves in the sites of the plurality of buildings and the factory 400, the number of counterparts with which the communication robot 110 can communicate is large so that a size of a counterpart database is large. Therefore, it takes time for the communication robot 110 to search for surrounding people or robots from the counterpart database, and there is a possibility that smooth communication with a counterpart is not performed in real time.

Therefore, the communication robot 110 registers, for example, a building name to which each counterpart belongs as a category as illustrated in FIG. 21, and updates category ranking information according to a position of the communication robot 110 as illustrated in FIG. 22. FIG. 21 is a table showing an example of a counterpart database 51a in the second modification. The counterpart database 51a stores an identification number (ID) of a counterpart, an image including a face, a name, and information regarding the counterpart such as a building to which the counterpart belongs as categories.

FIG. 22 is a table showing an example of the category ranking information stored in the storage 5. The category ranking information is updated in accordance with a change in the position of the communication robot 110. For example, when the communication robot 110 is in or near the building 401, the category ranking information is set to values shown in Table 50f. Thereafter, when the communication robot 110 moves to the inside of the building 402 or the vicinity thereof, the category ranking information is updated to values shown in Table 50g.

Furthermore, when a site of a building is large, the number of counterparts with which the communication robot 110 can communicate in the building is large so that a size of a counterpart database increases. In such a case as well, it takes time for the communication robot 110 to search for surrounding people or robots from the counterpart database, and there is a possibility that smooth communication with a counterpart is not performed in real time. Therefore, the categories may be further classified in detail and assigned to a plurality of zones in the building.

Since the category ranking information is appropriately set in accordance with the position of the communication robot 110 in this manner, the communication robot 110 can shorten the response time for detecting a counterpart, and can smoothly communicate with the counterpart.

4-3. Third Modification

Figure 23:
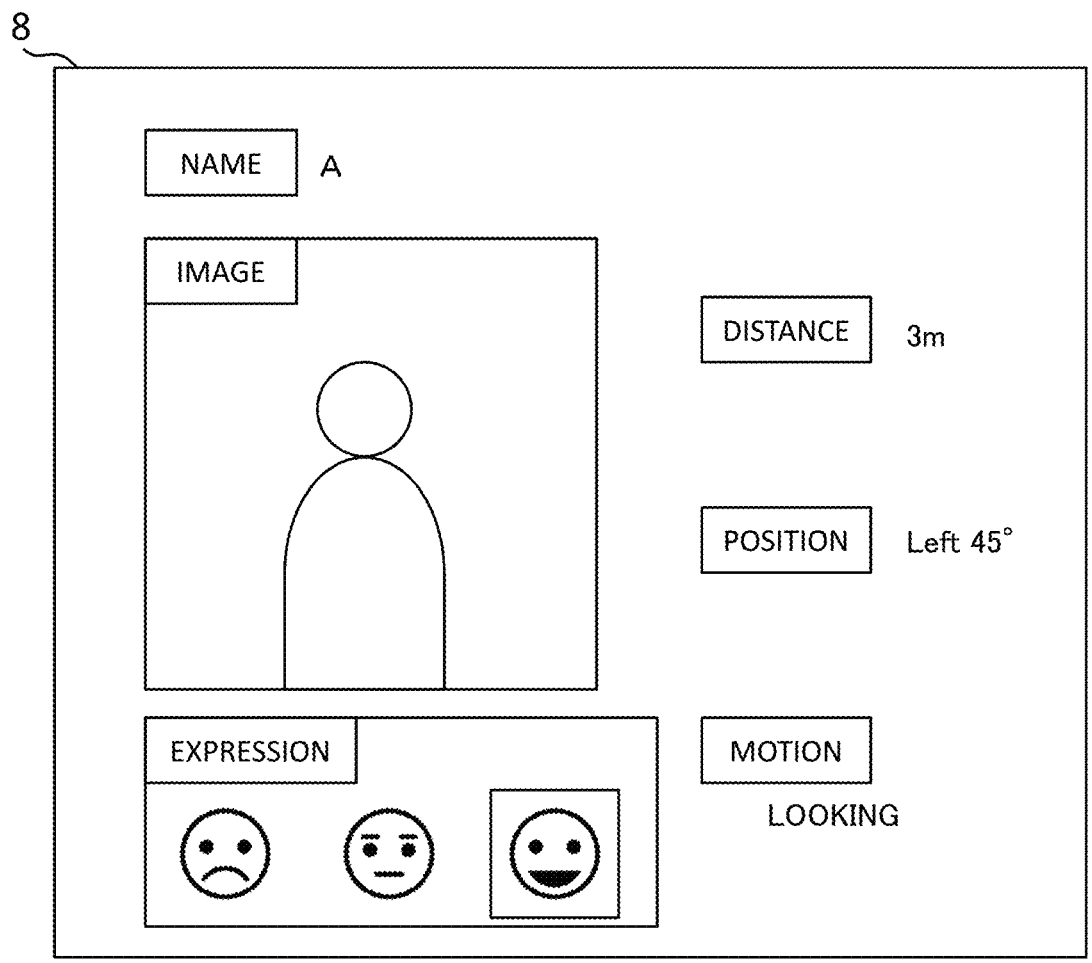
FIG. 23 is a schematic view illustrating a modification of an output mode of the communication support device according to the embodiment of the present disclosure.

FIG. 23 is a schematic view illustrating a modification of an output mode of the communication support device 100. In the above embodiment, the output mode of the communication support device 100 that provides communication support to the visually impaired user 90 has been described. As such an output mode, particularly, the notification unit 10 including the voice output unit 1 that performs voice notification and the vibration unit 2 that performs vibration notification has been described. The output mode of the present disclosure is not limited to these as long as information can be notified to the user 90. For example, the communication support device 100 may include a display 8 configured to visually notify the user 90.

For example, an image captured by the camera 3, a name of a counterpart, a distance from the camera 3 or the user 90 to the counterpart, and a position, a motion, and a facial expression of the counterpart are displayed on the display 8. As a result, the user 90 can quickly grasp the above information only by viewing the display 8 at a glance, and can smoothly communicate with the counterpart.

What is claimed is:

1. A communication support device comprising:
   a camera that captures an image of a surrounding environment of a user to acquire a captured image;
   a storage that stores a counterpart database in which an image of a counterpart and a category indicating a property of the counterpart are associated with the counterpart;
   a central processing unit (CPU) that:
      acquires position information indicating a position of a user;
      sets a priority to the category according to the position information;
      detects a counterpart belonging to the category in the captured image in order of the priority set by the category ranking setting unit;
      measures a distance between the counterpart and the camera based on the captured image;
      determines a facial expression of the counterpart based on the captured image; and
      determines a motion of the counterpart based on the captured image; and
   a notification unit that notifies the user of information regarding the counterpart detected by the counterpart detector,
   wherein the notification unit notifies the user of identification information for identifying the counterpart by a voice when the distance measured by the CPU is an interaction distance of a first threshold or less, and notifies the user of the identification information and at least one of facial expression information related to the facial expression determined by the CPU and motion information related to the motion determined by the motion determination unit by a voice when the distance measured by the distance measuring unit is longer than the first threshold.

2. The communication support device according to claim 1, wherein
   the notification unit
      notifies the user of the identification information and one of the facial expression information and the motion information when the distance measured by the CPU is a perceptual distance longer than the first threshold and equal to or less than a second threshold, and
      notifies the user of the facial expression information, the motion information, and the identification information when the distance measured by the CPU is an observation distance longer than the second threshold.

3. The communication support device according to claim 2, wherein
   the notification unit
      notifies the user of one of the facial expression information and the motion information by a voice after notifying the user of the identification information by a voice when the distance between the counterpart and the camera, measured by the CPU at a timepoint when detection has been performed by the counterpart detector, is the perceptual distance, and
      then, notifies the user of the other of the facial expression information and the motion information by a voice when the distance between the counterpart and the camera measured by the CPU is the perceptual distance.

4. The communication support device according to claim 1, further comprising a vibration unit that notifies the user of a detection result obtained by the CPU by a vibration,
   wherein the vibration unit changes at least one of a pattern and a magnitude of the vibration according to the distance between the counterpart and the camera detected by the CPU.

5. The communication support device according to claim 4, wherein
   the camera acquires a plurality of captured images by capturing an image of the surrounding environment of the user in a time-series manner,
   the communication support device further comprising a counterpart tracker that tracks the counterpart detected by the counterpart detector in the plurality of captured images,
   the vibration unit includes two or more vibrating elements capable of vibrating, and
   the vibration unit
      causes the respective vibrating elements to sequentially vibrate in a predetermined order when the distance between the counterpart and the camera detected by the CPU is a predetermined feedback distance in a case where the counterpart tracker tracks the counterpart, and
      causes the respective vibrating elements to sequentially vibrate in an order different from the predetermined order in a case where it is difficult for the counterpart tracker to track the counterpart that has been tracked.

6. The communication support device according to claim 5, wherein
the vibrating elements are three or more vibrating elements which are regularly arranged, and
the vibration unit
causes the respective vibrating elements to sequentially vibrate in an arranged order when the distance between the counterpart and the camera detected by the CPU is the feedback distance in the case where the counterpart tracker tracks the counterpart, and
causes the respective vibrating elements to sequentially vibrate in a reverse order of the arranged order in the case where it is difficult for the counterpart tracker to track the counterpart that has been tracked.

7. The communication support device according to claim 5, further comprising a counterpart position detector that detects a position of the counterpart with respect to the camera based on the captured image,
wherein the vibrating elements include a right vibrating element and a left vibrating element, and
the vibration unit causes the right vibrating element to vibrate when the position of the counterpart with respect to the camera detected by the counterpart position detector is a right side of an optical axis of the camera, and causes the left vibrating element to vibrate when the position of the counterpart is a left side of the optical axis of the camera.

8. A communication support method comprising:
acquiring, by a central processing unit (CPU), position information indicating a position of a user;
causing, by the CPU, a camera to capture an image of a surrounding environment of the user to acquire a captured image;
acquiring, by the CPU, a counterpart database in which an image of a counterpart and a category indicating a property of the counterpart are associated with the counterpart, from a storage;
setting, by the CPU, a priority to the category according to the position information;
detecting, by the CPU, a counterpart belonging to the category in the captured image in order of the priority set by the category ranking setting unit;
measuring, by the CPU, a distance between the counterpart and the camera based on the captured image;
determining, by the CPU, a facial expression of the counterpart based on the captured image;
determining, by the CPU, a motion of the counterpart based on the captured image; and
causing, by the CPU, a notification unit to notify the user of information regarding the counterpart detected by the counterpart detector
wherein the notification unit notifies the user of identification information for identifying the counterpart by a voice when the distance measured by the CPU is an interaction distance of a first threshold or less, and notifies the user of the identification information and at least one of facial expression information related to the facial expression determined by the CPU and motion information related to the motion determined by the motion determination unit by a voice when the distance measured by the distance measuring unit is longer than the first threshold.

9. A computer-readable storage medium including a program for causing a computer to execute the communication support method according to claim 8.

* * * * *

UNITED STATES PATENT AND TRADEMARK OFFICE
CERTIFICATE OF CORRECTION

PATENT NO. : 11,954,908 B2
APPLICATION NO. : 17/391615
DATED : April 9, 2024
INVENTOR(S) : Rama et al.

It is certified that error appears in the above-identified patent and that said Letters Patent is hereby corrected as shown below:

On the Title Page

Item (72) Second Inventor, Kazuo, YAMAMOTO's residence is Nara (JP).

Signed and Sealed this
Twenty-eighth Day of May, 2024

Katherine Kelly Vidal
*Director of the United States Patent and Trademark Office*